(12) United States Patent
Khater

(10) Patent No.: US 12,023,185 B2
(45) Date of Patent: Jul. 2, 2024

(54) POSITIONING SYSTEM

(71) Applicant: Saint Louis University, St. Louis, MO (US)

(72) Inventor: Nabil Khater, Wildwood, MO (US)

(73) Assignee: Saint Louis University, St. Louis, MO (US)

( * ) Notice: Subject to any disclaimer, the term of this patent is extended or adjusted under 35 U.S.C. 154(b) by 49 days.

(21) Appl. No.: 17/173,951

(22) Filed: Feb. 11, 2021

(65) Prior Publication Data

US 2021/0244368 A1 Aug. 12, 2021

Related U.S. Application Data

(60) Provisional application No. 62/972,887, filed on Feb. 11, 2020.

(51) Int. Cl.
*A61B 6/04* (2006.01)
*A61G 7/10* (2006.01)
(Continued)

(52) U.S. Cl.
CPC .......... *A61B 6/0407* (2013.01); *A61B 6/0485* (2013.01); *A61G 13/121* (2013.01); *A61G 13/122* (2013.01); *A61G 13/1225* (2013.01); *A61G 13/1265* (2013.01); *A47G 9/1027* (2013.01); *A61G 7/1021* (2013.01)

(58) Field of Classification Search
CPC ..... A61B 6/0485; A61B 6/0407; A61B 6/501; A61G 13/1265; A61G 13/1275; A61G 13/121; A61G 13/122; A61G 13/1225; A61G 13/126; A61G 13/12; A61G 13/1205; A61G 13/02; A61G 15/125; A61G 13/123; A61G 7/065; A61G 7/07; A61G 7/072; A61G 7/05769; A61G 7/05776; A61G 7/1021; A61G 2210/50; A47G 9/1027; A47G 2009/003; A47C 20/027; A47C 27/084; A47C 27/10; A47C 27/18

See application file for complete search history.

(56) References Cited

U.S. PATENT DOCUMENTS 3,266,061 A * 8/1966 Fuechsel ................ A47C 1/143
5/725
4,710,991 A 12/1987 Wilmore et al.
(Continued)

FOREIGN PATENT DOCUMENTS

EP 2116155 A1 * 11/2009 ............ A47G 9/1027
KR 101840442 B1 * 3/2018 ............ A47G 9/1027
WO WO-2019183293 A1 * 9/2019 ............ A61G 13/121

OTHER PUBLICATIONS

Bentel G. C., et al. "A Customized Head and Neck Support System" (1995). Int. J. Radiation Oncology Biol. Phys., 32/1: 245-248, 4 pages.
(Continued)

*Primary Examiner* — David R Hare
*Assistant Examiner* — Deborah Talitha Gedeon
(74) *Attorney, Agent, or Firm* — Stinson LLP

(57) ABSTRACT

The present disclosure relates to a system for positioning a patient on a medical device. More specifically, the present disclosure relates to a system for aligning a patient's head, spine, and shoulders for providing radiation treatment to a head and neck area of the patient.

18 Claims, 33 Drawing Sheets

(51) Int. Cl.
*A61G 13/12* (2006.01)
*A47G 9/10* (2006.01)

(56) References Cited

U.S. PATENT DOCUMENTS

| | | | | |
|---|---|---|---|---|
| 4,805,603 | A * | 2/1989 | Cumberland | A61H 1/0218 128/DIG. 20 |
| 4,893,367 | A | 1/1990 | Heimreid et al. | |
| 5,461,741 | A * | 10/1995 | Graebe | A47C 27/10 297/284.6 |
| 6,357,066 | B1 * | 3/2002 | Pierce | A61B 6/0442 5/713 |
| 6,848,134 | B1 * | 2/2005 | Schenck | A61G 1/00 5/632 |
| 7,213,596 | B2 | 5/2007 | Saied | |
| 7,437,789 | B2 * | 10/2008 | Thompson | A47C 7/467 5/644 |
| 7,451,507 | B2 | 11/2008 | Brinkerhoff et al. | |
| 7,555,794 | B2 | 7/2009 | Zelnik et al. | |
| 8,093,569 | B2 | 1/2012 | Miller et al. | |
| 8,176,585 | B1 * | 5/2012 | Isham | A61G 13/123 5/710 |
| 8,607,385 | B2 | 12/2013 | Isham | |
| 9,474,672 | B2 * | 10/2016 | Robran | A61F 5/01 |
| 10,448,746 | B2 * | 10/2019 | Galloway | A47C 20/027 |
| 2011/0185503 | A1 * | 8/2011 | Yan | A61N 5/1049 5/601 |
| 2012/0079660 | A1 * | 4/2012 | Chen | A47G 9/10 5/644 |
| 2012/0305007 | A1 | 12/2012 | Yan | |
| 2021/0330102 | A1 * | 10/2021 | Monico | A47G 9/1054 |

OTHER PUBLICATIONS

Chen, A. M., et al., "Marginal Misses After Postoperative Intensity-Modulated Radiotherapy for Head and Neck Cancer," 2011, Int. J. Radiation Oncology Biol Phys, 80/5:1423-1429, Abstact Only, 2 pages.

Chen, A. M., et al., "Hazards of Sparing the Ipsilateral Parotid Gland in the Node-Positive Neck with Intensity Modulated Radiation Therapy: Spatial analysis of Regional Recurrence Risk," 2018, Adv. Radiation Oncol, 14/3 (2):111-120, 10 pages.

Ezzell, L. C., et al., "Detection of Treatment Setup Errors Between Two CT Scans for Patients with Head and Neck Cancer,", 2007, Med Phys, 34/8:3233-3242, Abstract Only, 1 page.

Jemal, A., et al., "Global Cancer Statistics," 2011, CA Cancer J Clin, 61/2:69-90, 22 pages.

Lee, H-T., et al., "Shape Memory Alloy (SMA)-Based Head and Neck Immobilizer for Radiotherapy," 2015, J Computational Design and Engineering, 2:176-192, 7 pages.

Ogunmolu, O., et al., "Soft-NeuroAdapt: A 3-DOF Neuro-Adaptive Patient Pose Correction System for Frameless and Maskless Cancer Radiotherapy, " 2017, IEEE/RSJ Int'l. Conf. on Intelligent Robots and Systems (IROS), Sep. 24-28, 2017, Vancouver, BC, Canada, 8 pages.

Ogunmolu, O.P., et al., "Vision-Based Control of a Soft Robot for Maskless Head and Neck Cancer Radiotherapy," 2016, IEEE Int'l. Conf. on Automation Sci. and Engineering (CASE), Aug. 21-24, 2016, Fort Worth, TX, 8 pages.

Ogunmolu, O.P., et al., "A Real-Time, Soft Robotic Patient Positioning System for Maskless Head-and-Neck Cancer Radiotherapy: An Initial Investigation," 2015, IEEE Int'l. Conf. on Automation Sci and Engineering (CASE), Aug. 24-28, 2015, Gothenburg, Sweden, 7 Pages.

Sanguineti, G., et al., "Patterns of locoregional Failure After Exclusive IMRT for Oropharyngeal Carcinoma," 2008, Int. J. Radiation Biol. Phys, 72/3:737-746, Abstract Only, 1 page.

\* cited by examiner

POSITIONING SYSTEM

CROSS REFERENCE TO RELATED APPLICATIONS

This application claims priority to U.S. provisional application No. 62/972,887, filed Feb. 11, 2020, the entire disclosure of which is incorporated by reference.

FIELD

The present disclosure relates to a system for positioning a patient on a medical device. More specifically, the present disclosure relates to a system for aligning a patient's head, spine and shoulders for providing radiation treatment to a head and neck area of the patient.

BACKGROUND

Radiation therapy is an essential treatment method for head and neck cancer (HNC). The annual incidence of head and neck cancers worldwide is more than 550,000 cases with around 300,000 deaths each year. Historically and prior to the adoption of intensity modulated radiation therapy (IMRT) and volumetric modulated arc therapy (VMAT), an improved format of IMRT, HNC patients were treated with a 3D conformal radiation therapy (3DCRT) technique. 3DCRT utilizes conservatively large fields, defined clinically based on anatomical knowledge, and are less susceptible to errors resulting from repositioning uncertainties and anatomical changes during the course of therapy. The downside of 3DCRT are toxicities of normal tissues surrounding the cancer. The primary organs at risk (OAR) in HNC are the parotids. One of the most common and serious side effects of HNC treatment with 3DCRT is the loss of salivary function. The IMRT or VMAT techniques, used interchangeably hereinafter, can reduce those side effects drastically and allows the patients to retain some or all of their salivary functions after the treatment is completed. IMRT is planned and delivered after precise delineation of all anatomical organs on the reference computed tomography (CT) scan commonly known as the simulation or reference scan or image. Such anatomical organs would include all possible OARs in addition to the gross tumor volume(s) (GTVs), the clinical target volume(s) (CTVs) representing areas of gross and suspected subclinical disease, and their corresponding planning target volumes (PTVs) representing an expansion of the CTVs by a margin on the order of 5 millimeters. Such margin is placed to account for uncertainties in daily positioning. The treatment planning for such cases will tightly shape the radiation dose to the PTVs and would maximize the sparing of the OARs, hence, the reduced sequela resulting from radiation therapy.

Currently, IMRT is the standard treatment modality for HNC. The primary disease area may be the nasopharynx, oropharynx, tonsil(s), larynx, tongue, sinus or other organs, but the treatment area may extend to the neck lymphatic chain all the way down to the supraclavicular level. For such cases, daily repositioning variations are observed consistently due to the flexible nature of the cervical vertebrae and shoulders. With some patients, this variability is more pronounced for various reasons (e.g., higher body mass index, changes in body mass, general patient positioning discomfort). Therapy delivery systems offer advanced integrated imaging and repositioning tools, but such systems are not successful in mitigating the cervical vertebrae variations. Cone beam computed tomography (CBCT) in conjunction with a robotic six-degree-of-freedom couch (6DOF couch) are capable of producing a repositioning correction in 3 translations and 3 rotations. However, they work under the conditions of rigid transformations, hence they are not capable of accounting for the error produced by the cervical vertebrae flexure and shoulder misalignments. A rigid registration using a region of interest (ROI) near the primary disease site (superior part of the field for example) would correct for that site but may cause severe offsets in the supraclavicular area (inferior part of the field); and vice versa. Incorrect daily repositioning of the patient could result in marginal miss of the PTVs which may lead to a less than optimal therapy outcome. There exists a need in HNC treatments for a mechanism to correct the deformation of the cervical vertebrae flexure prior to treatment.

SUMMARY

In one aspect, a positioning system for positioning a patient for therapy generally comprises a support plate including a bottom surface for engaging a support surface to locate the support plate for therapy, and an upper surface. A headrest assembly is mounted on the upper surface of the support plate for supporting a head and neck area of the patient. The headrest assembly includes a plurality of inflatable bladders for adjusting a position of the patient's head, neck and shoulders to selectively position the patient's head and neck for therapy.

In another aspect, a positioning system for positioning a patient for therapy generally comprises a support plate including a bottom surface for engaging a support surface to locate the support plate for therapy, and an upper surface. A headrest is mounted on the upper surface of the support plate for supporting a head and neck area of the patient. The headrest comprises an elongate frame member defining a plurality of support surfaces longitudinally spaced along the elongate frame member. The elongate frame member includes a top section, a middle section, and a bottom section. The top section is configured to support the patient's head. The middle section is configured to support the patient's neck. The bottom section is configured to support the patient's lower neck and upper T-spine.

In yet another aspect, a method for positioning a patient for radiation therapy generally comprises supporting a patient's head, neck, and shoulder area in a radiation therapy device. The method further comprise selectively adjusting a position of the patient's head, neck, and shoulder area using a plurality of inflatable bladders to reproduce patient head and neck positioning for image-guided radiotherapy (IGRT) of the patient's head and neck area.

BRIEF DESCRIPTION OF THE DRAWINGS

Various embodiments of the presently disclosed positioning system are described herein with reference to the drawings, wherein.

DETAILED DESCRIPTION OF EMBODIMENTS

Figure 1:
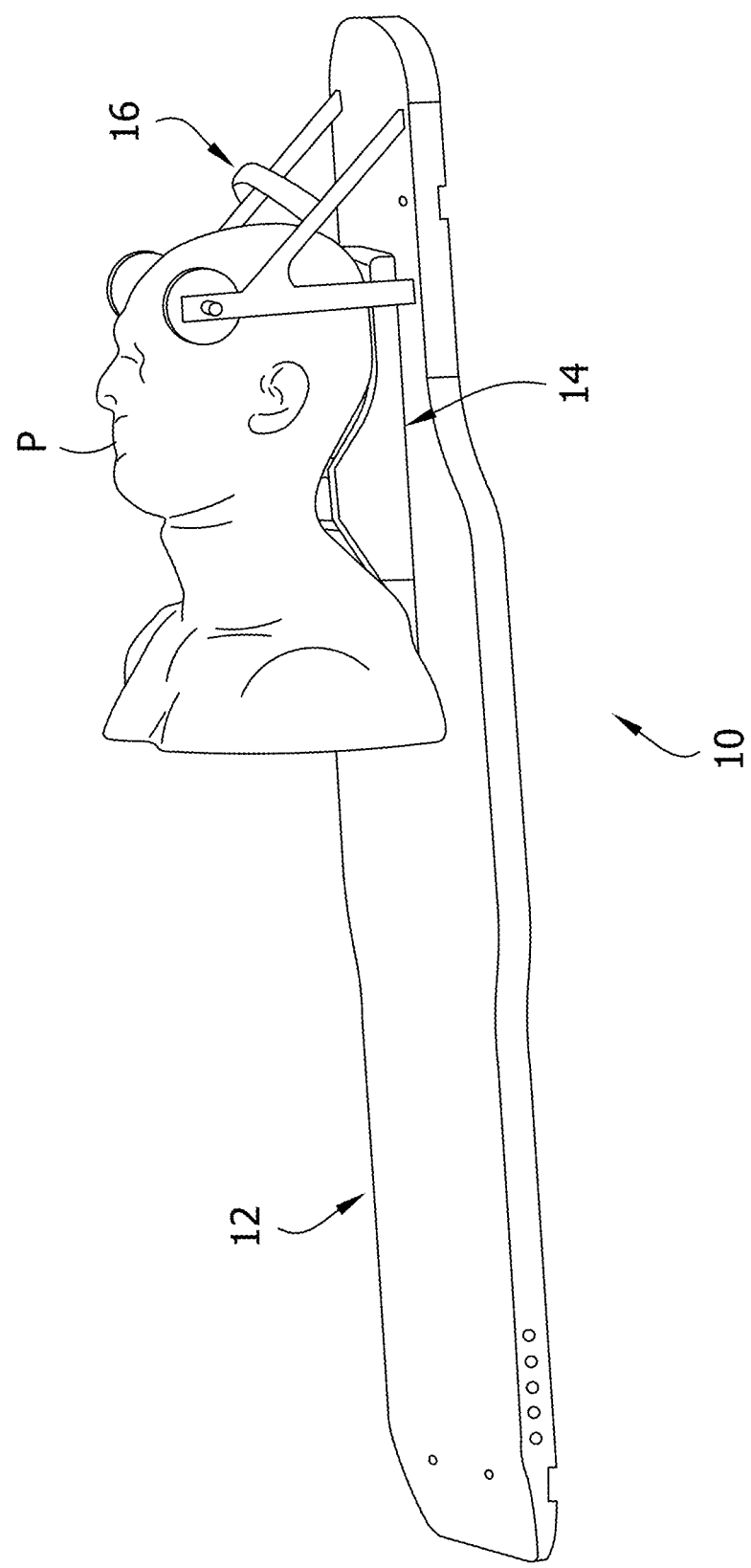
FIG. 1 is a perspective view of a patient positioning system with an illustration of a patient's head, neck, and upper torso being supported on the patient positioning system.
Figure 2:
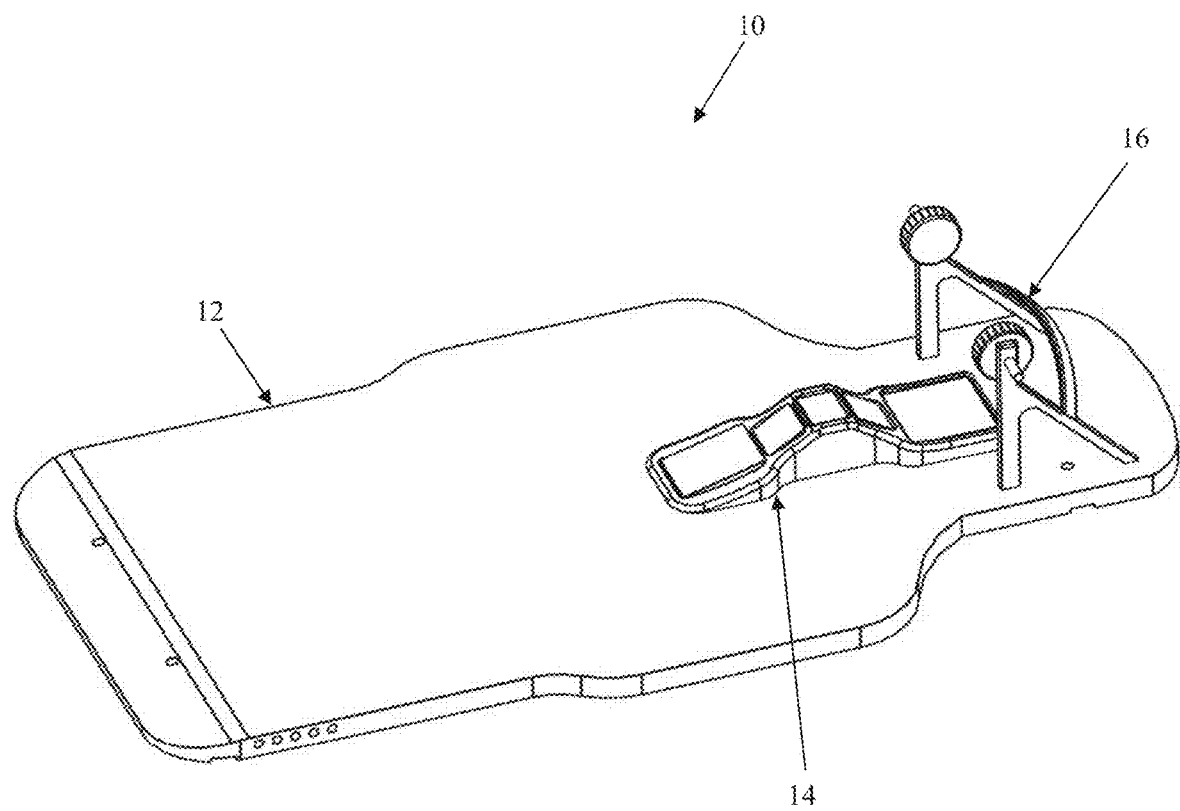
FIG. 2 is a perspective view of the patient positioning system.
Figure 3:
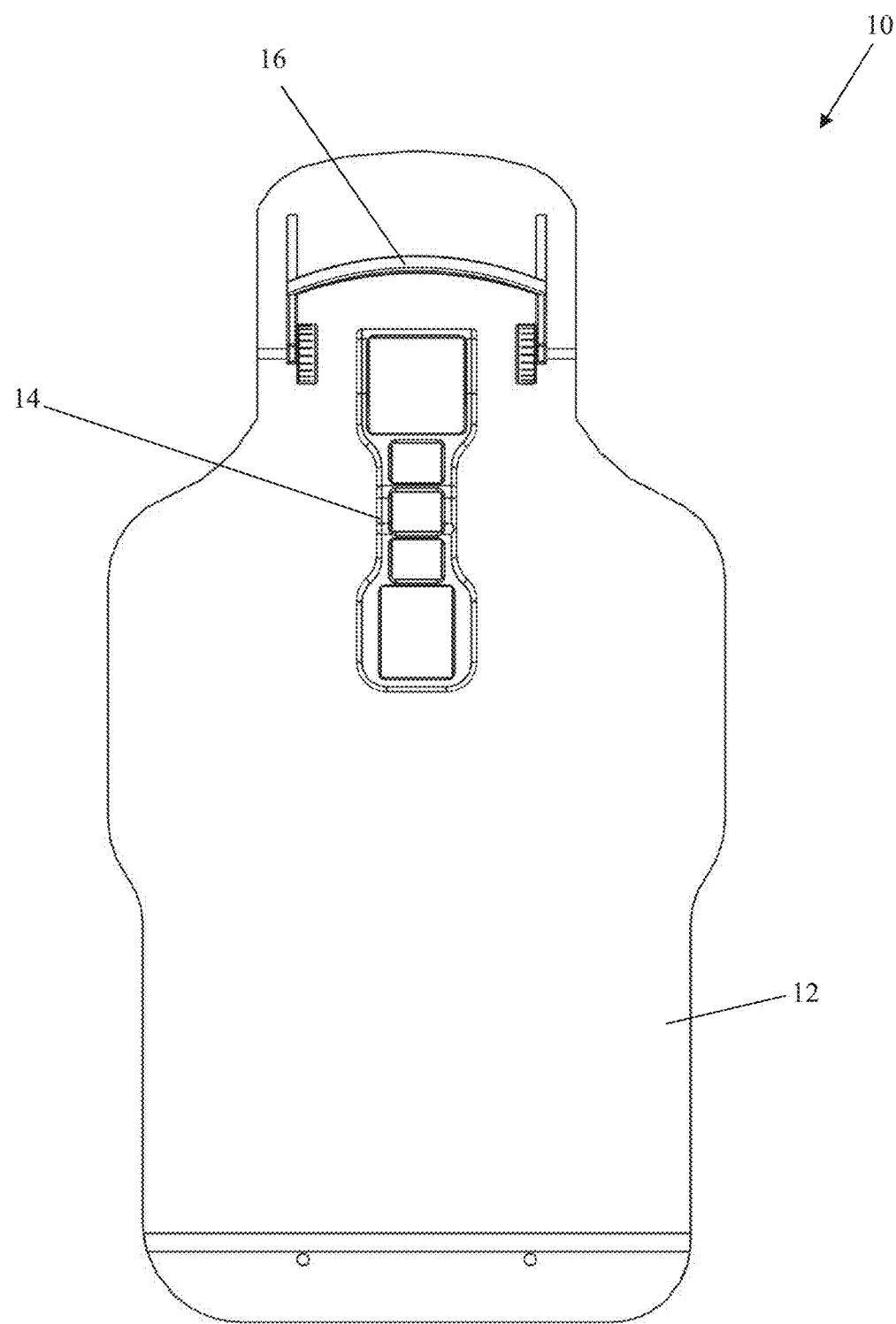
FIG. 3 is a top plan view of the patient positioning system.
Figure 4:
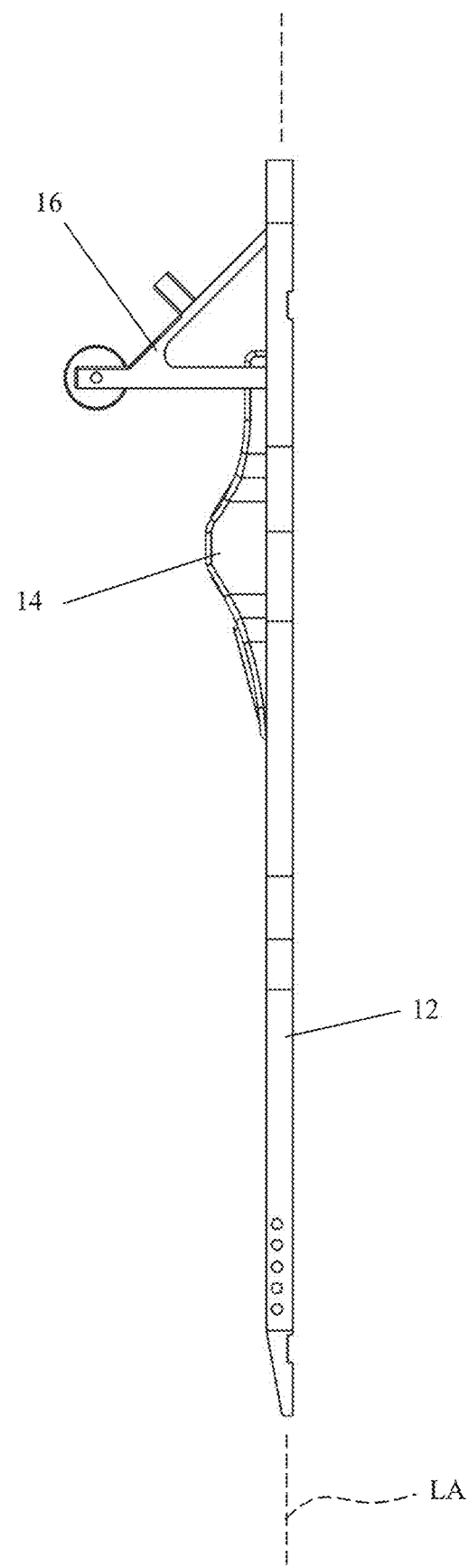
FIG. 4 is a side view of the patient positioning system.
Figure 5:
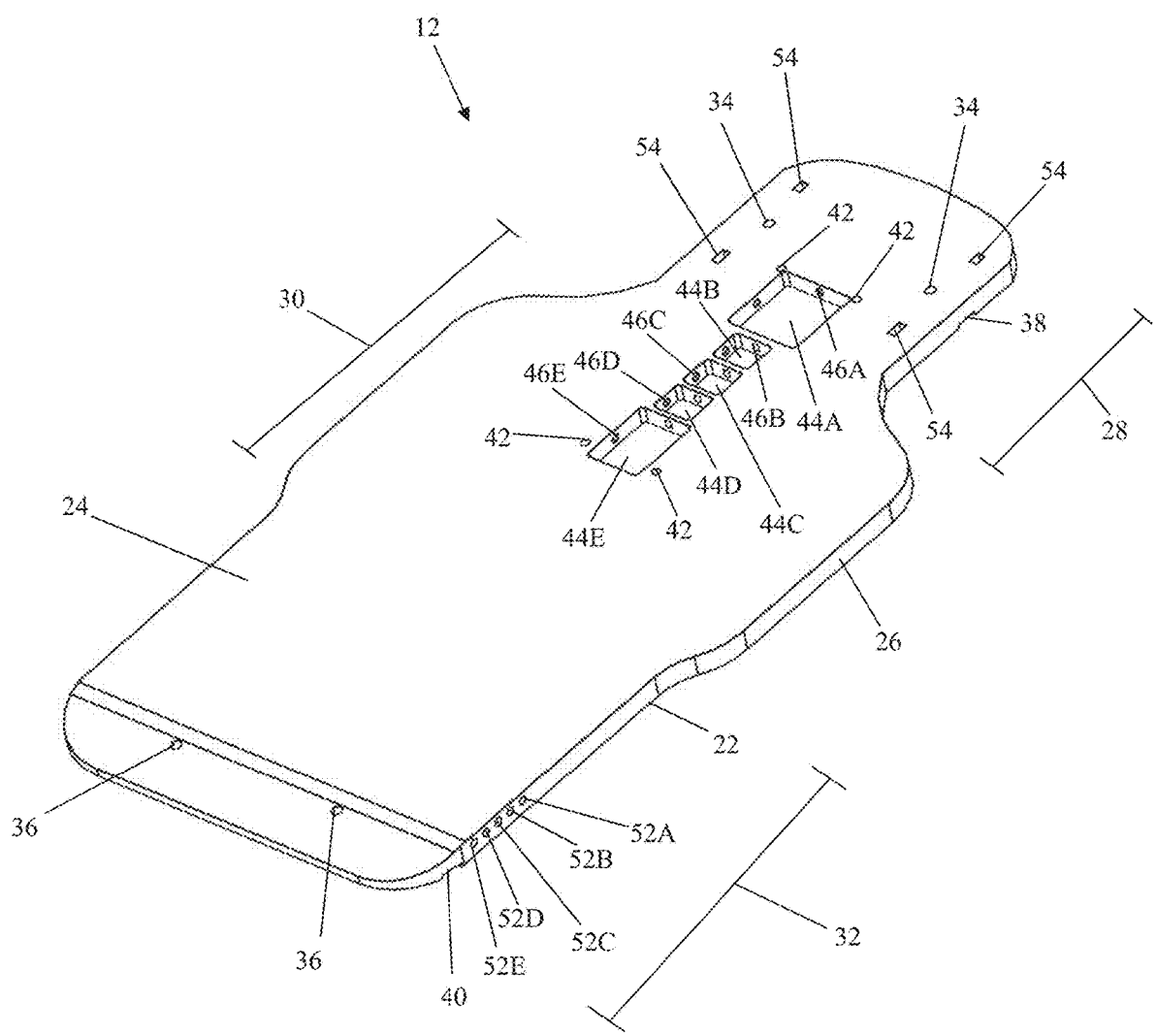
FIG. 5 is a top perspective view of a support plate of the patient positioning system.
Figure 6:
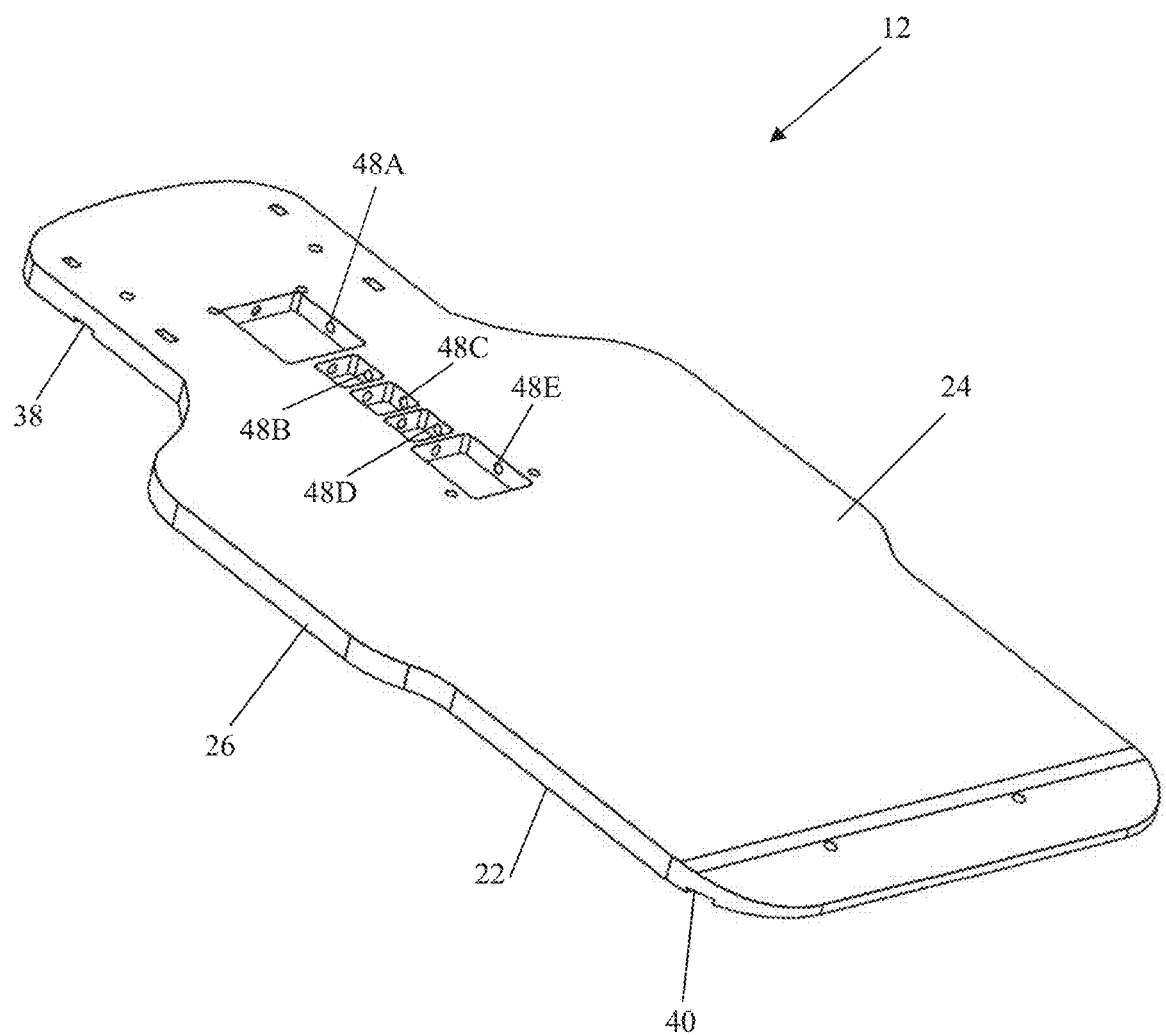
FIG. 6 is another top perspective view of a support plate of the patient positioning system.
Figure 7:
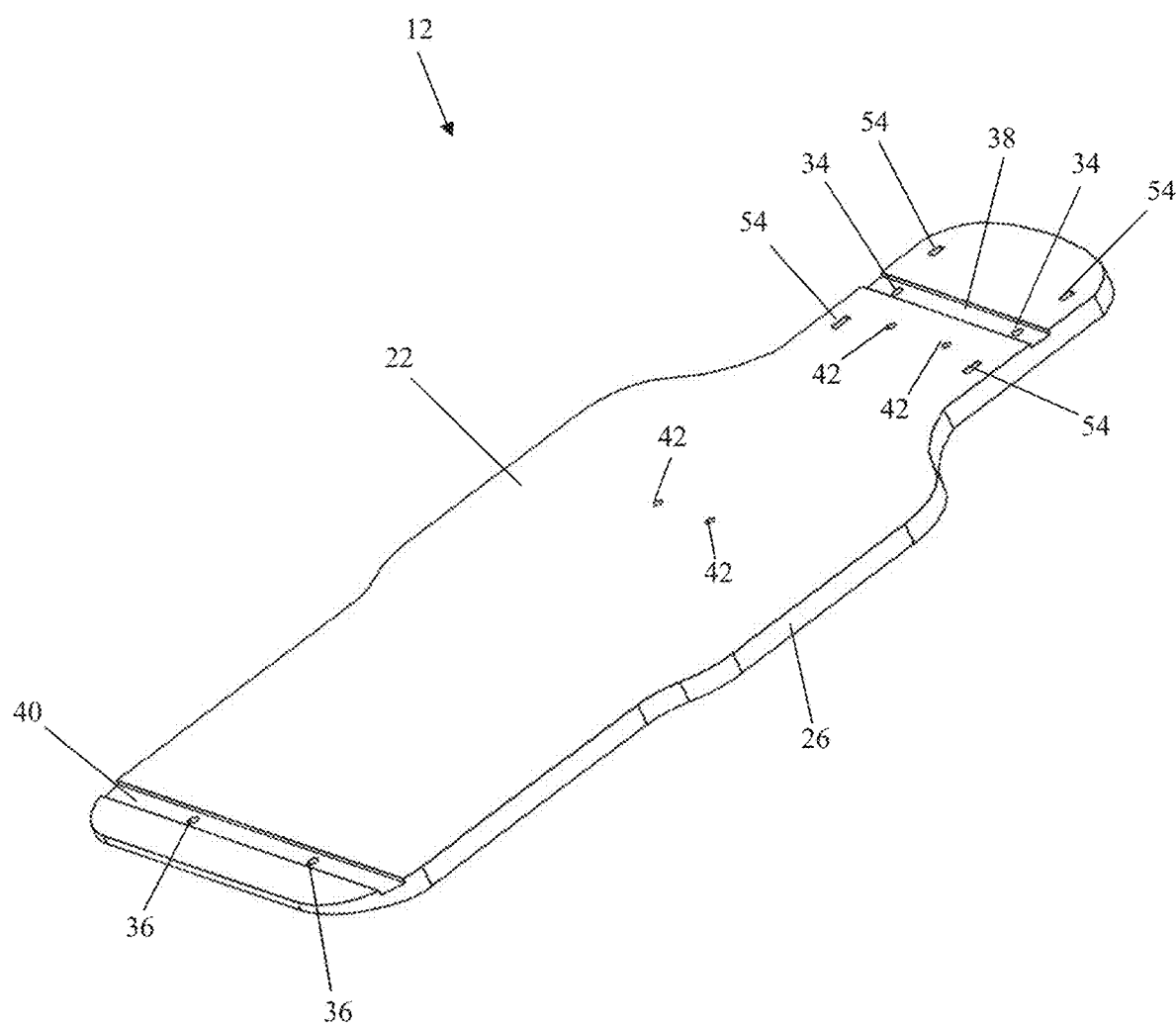
FIG. 7 is a bottom perspective view of a support plate of the patient positioning system.
Figure 8:
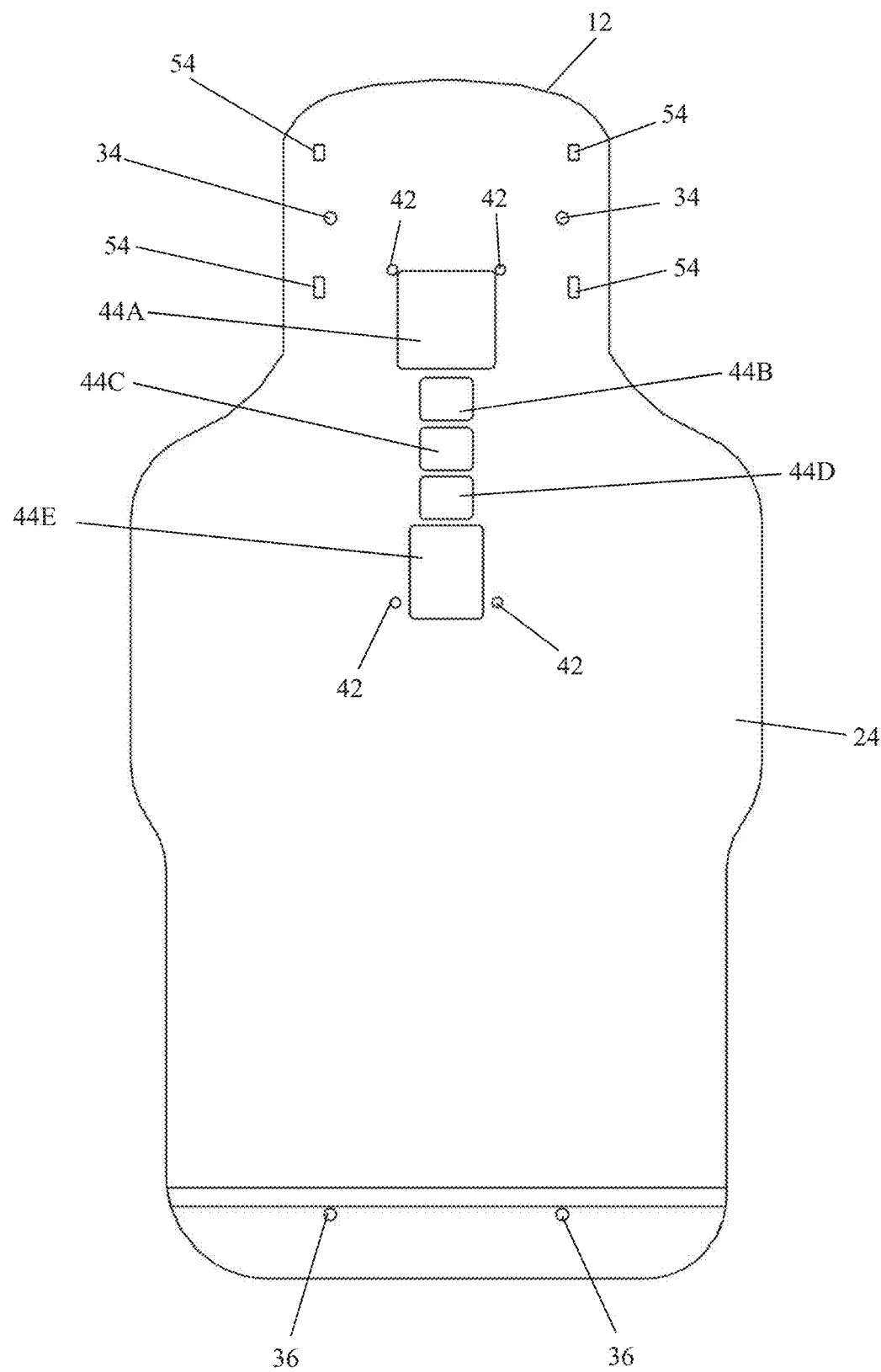
FIG. 8 is a top plan view of the support plate.
Figure 9:
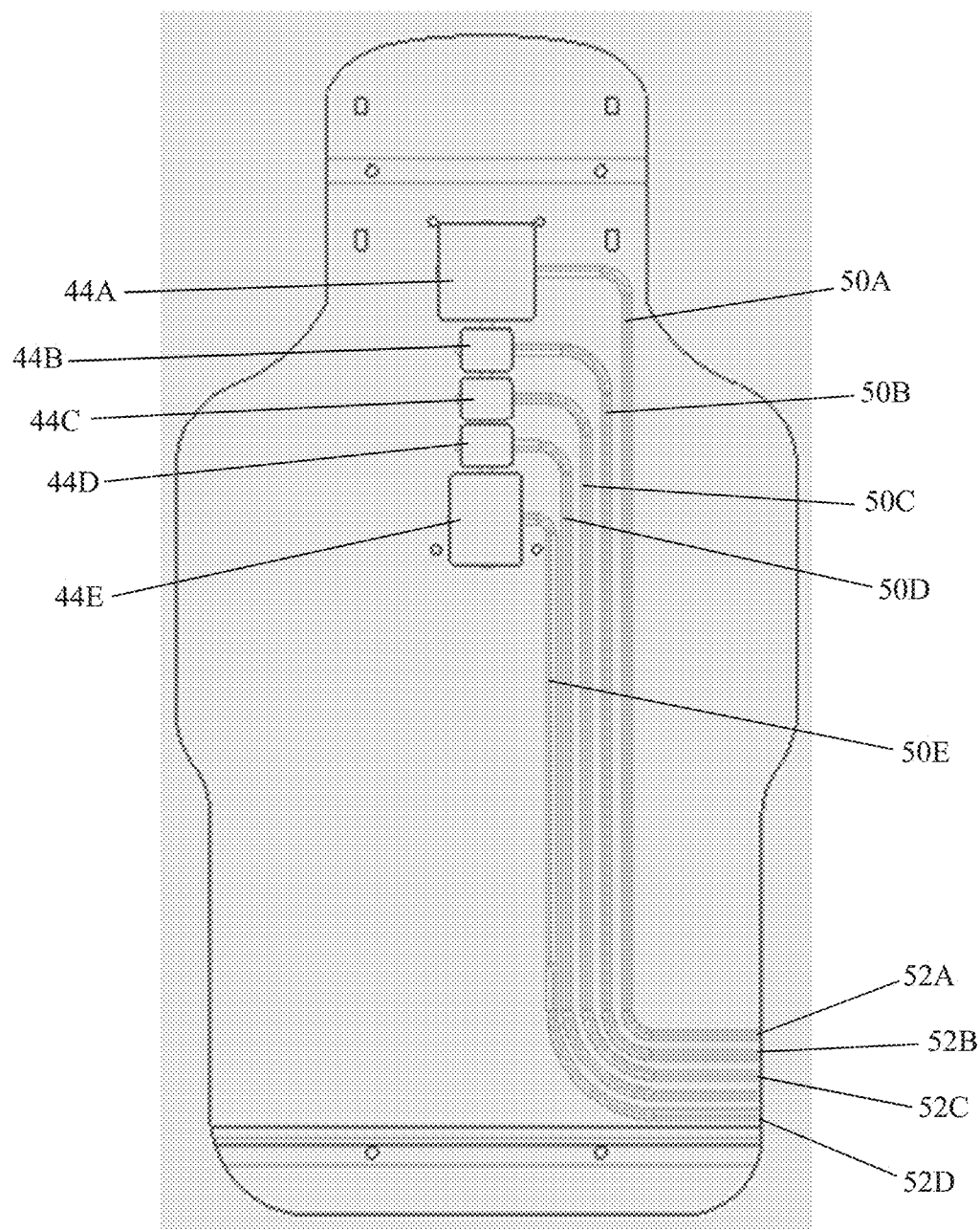
FIG. 9 is a section of the support plate.
Figure 10:
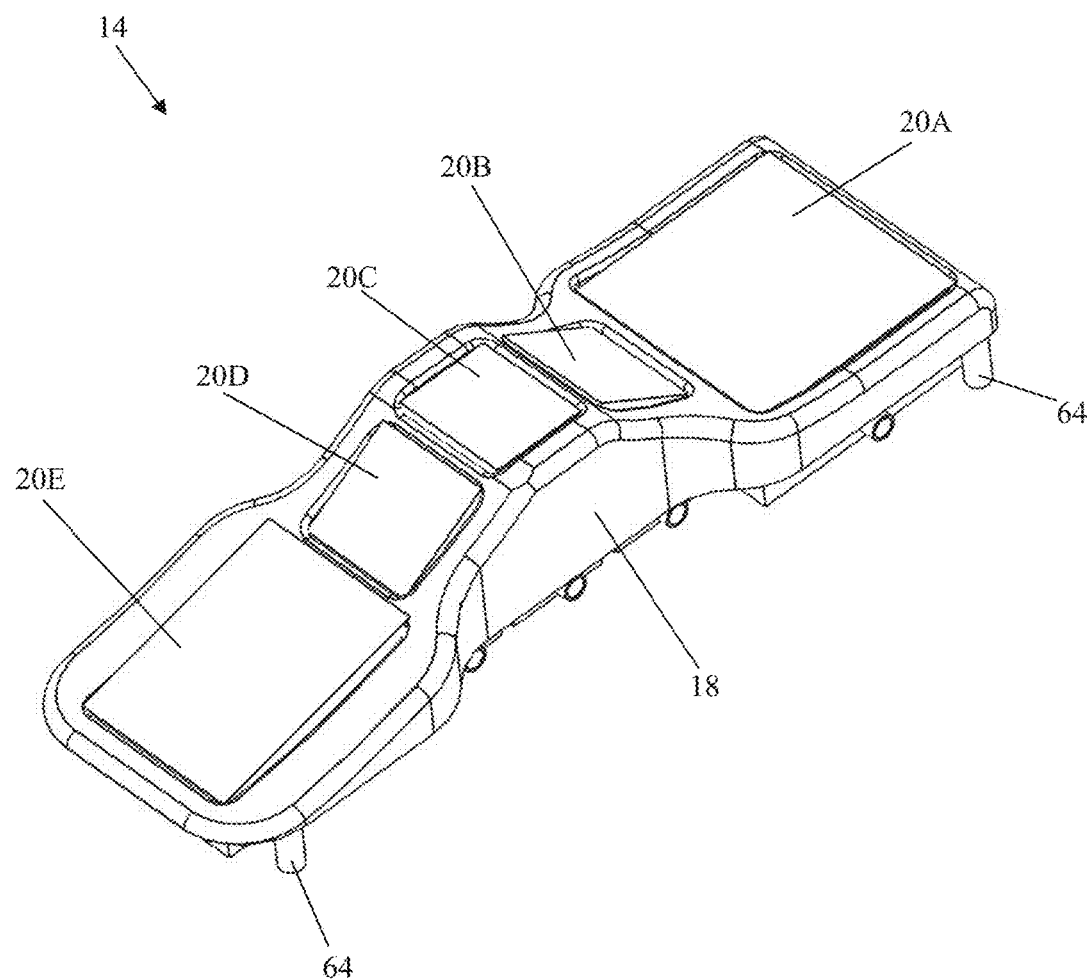
FIG. 10 is a perspective view of a headrest assembly of the patient positioning system.
Figure 11:
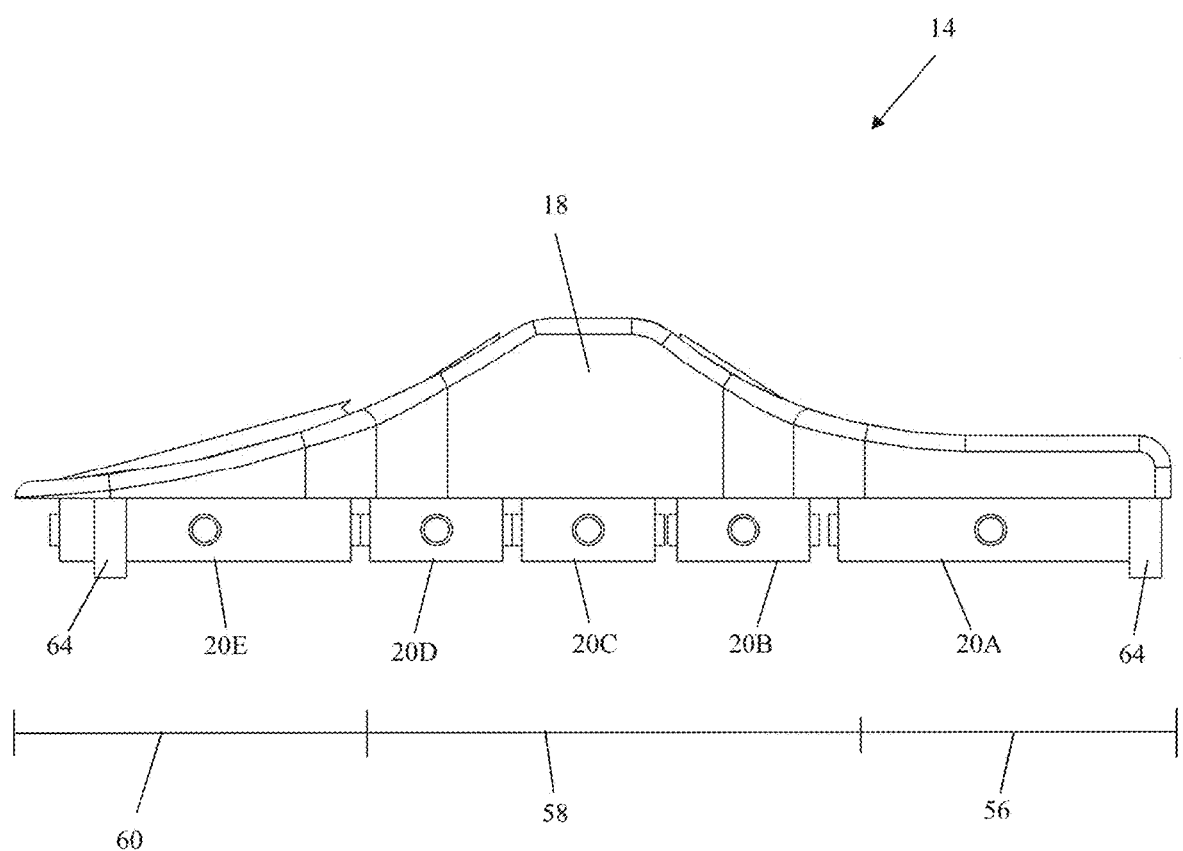
FIG. 11 is a side view of the headrest assembly.
Figure 12:
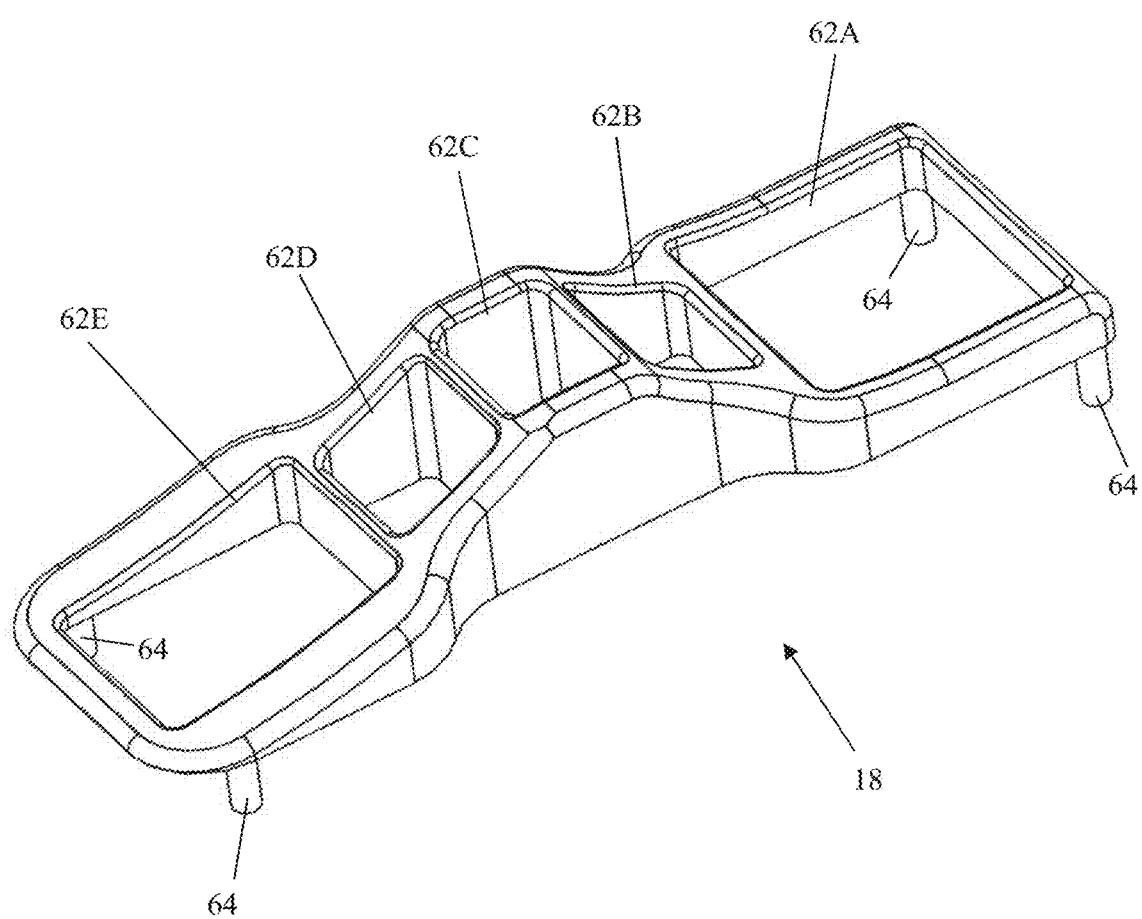
FIG. 12 is a perspective view of a headrest of the headrest assembly.
Figure 13:
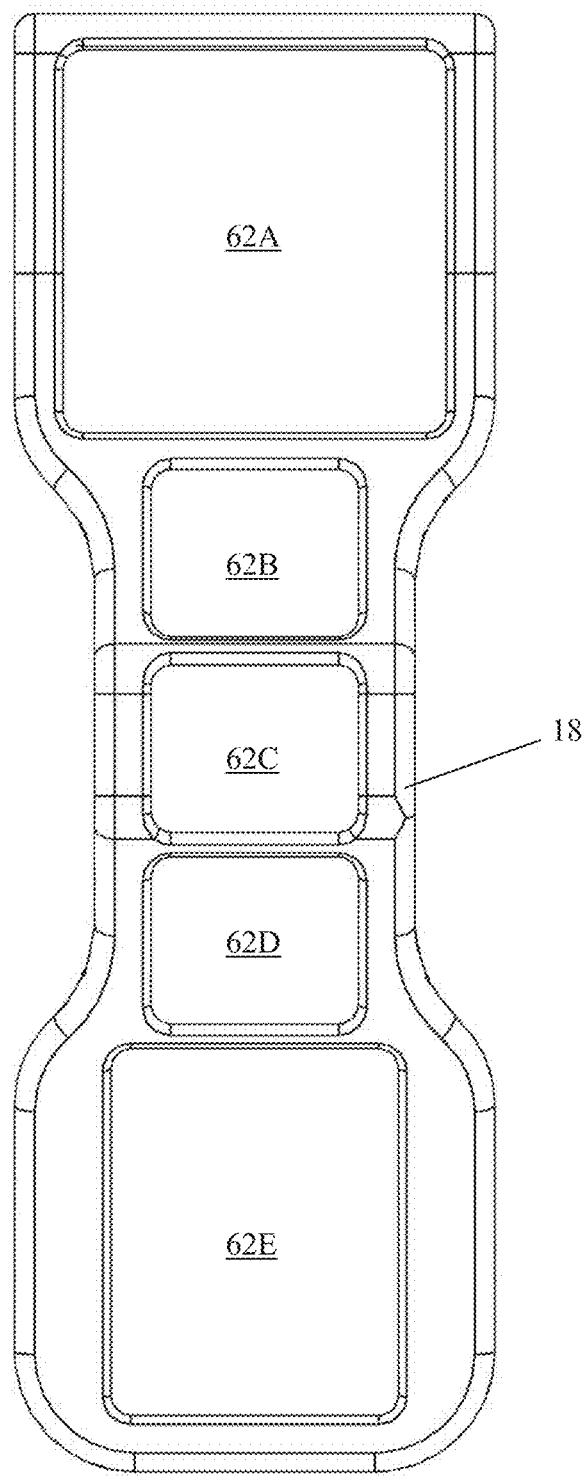
FIG. 13 is a top plan view of the headrest.
Figure 14:
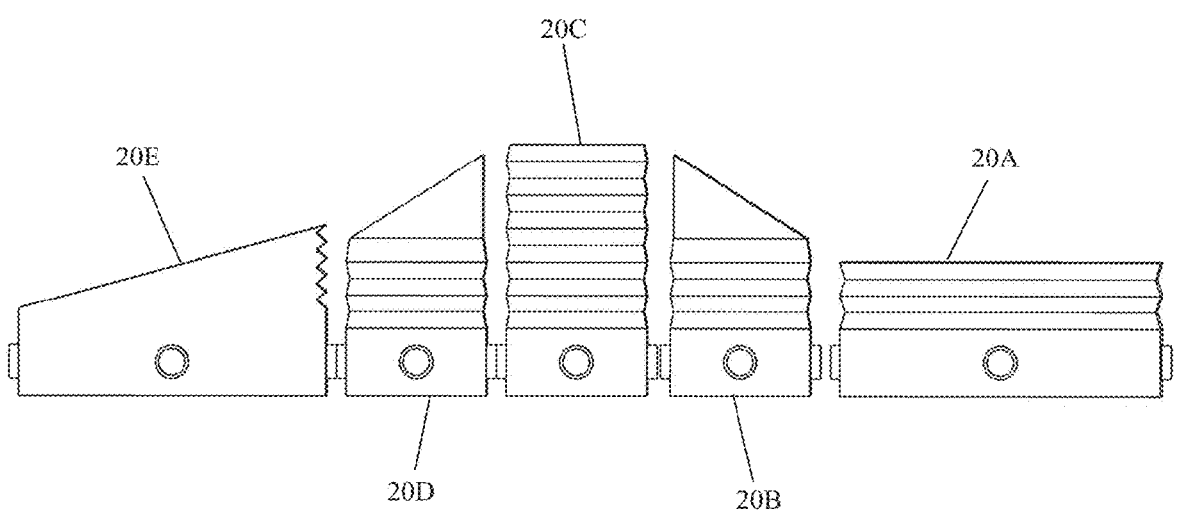
FIG. 14 is a side view of bladders of the headrest assembly.
Figure 15A:
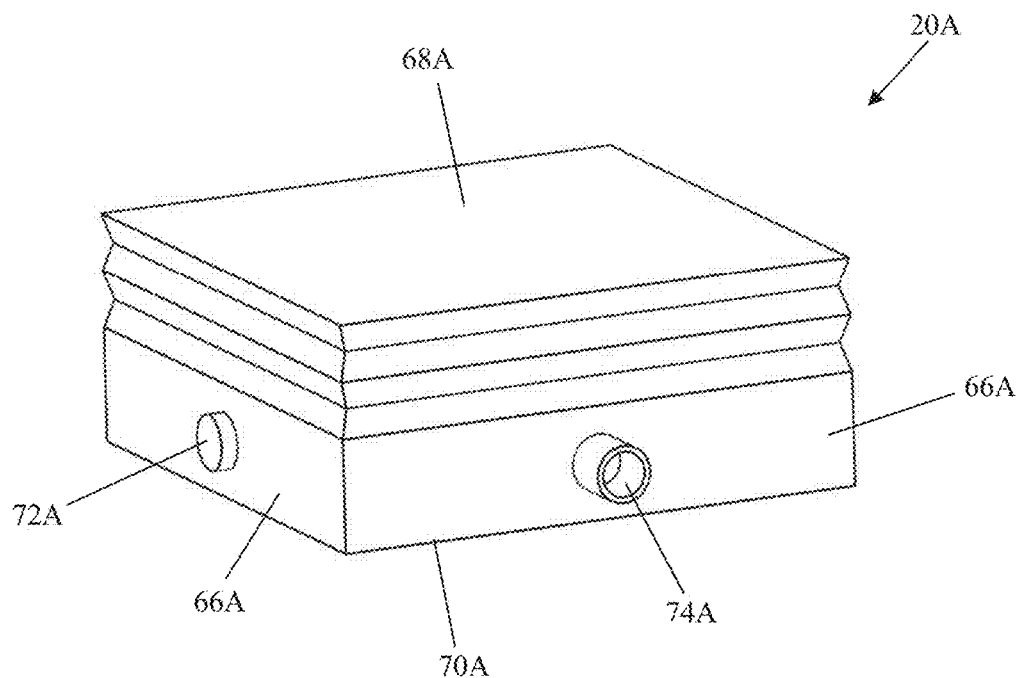
FIGS. 15A and 15B are perspective views of a first bladder.
Figure 15B:
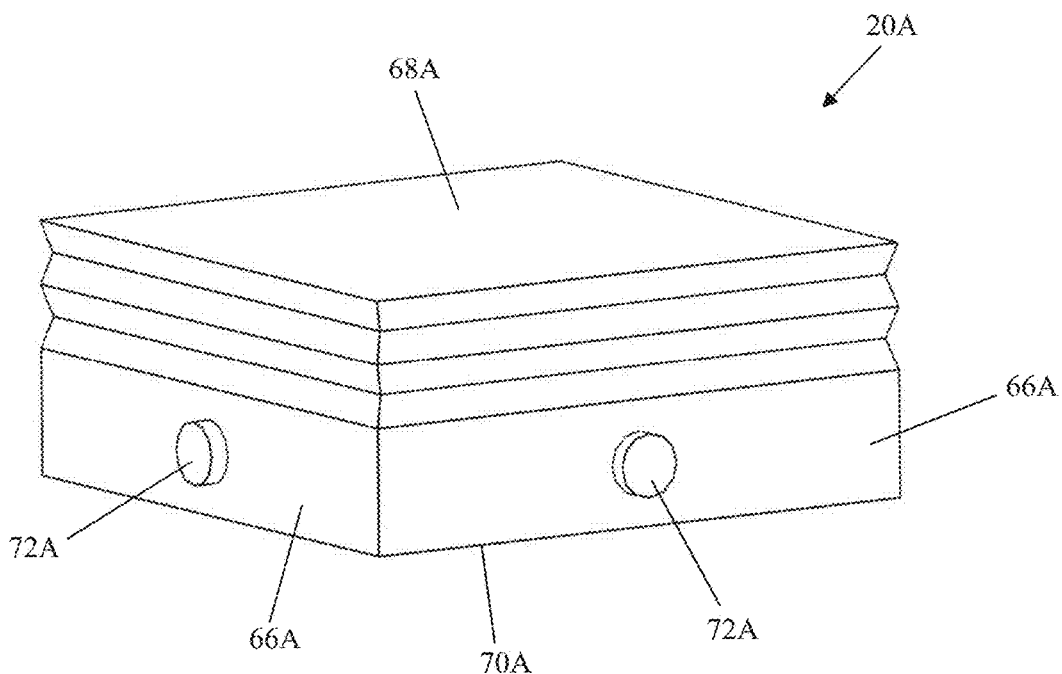

Referring to FIGS. 1-4, the presently disclosed patient positioning system, shown generally as 10, includes a support plate 12 for supporting a patient P in a diagnostic/therapy device (e.g., CT scanner/radiation therapy machine), a headrest assembly 14 for supporting and adjusting a position of the patient's head and neck area on the support plate, and a head frame assembly 16 mounted on the support plate for limiting roll movement of the patient's head. As will be explained in greater detail below, the headrest assembly 14 comprises a headrest 18 and a plurality of inflatable bladders 20A-E (FIG. 10) and is configured to adjust the position of the patient's head, spine flexure (e.g., cervical vertebrae), and supraclavicular positions during pre-treatment setup to match reference or simulation positions thereby providing a system that allows for reproducing patient head and neck positioning for image-guided radiotherapy (IGRT) such as for the treatment of head and neck cancers. Being able to match the bony imaging of the non-rigid anatomy of a patient's head and neck area with reference imaging reduces positional uncertainties in IGRT; such uncertainties can result in local and regional cancer recurrences within the patient. Thus, the patient positioning system 10 mitigates the repositioning errors of the head, cervical vertebrae and shoulders, hence enabling better local/regional control of the cancer through the accurate targeting of all planning target volumes (PTVs) and the accurate sparing of organs at risk (OARs). The patient positioning system 10 can also be used in combination with other cancer therapy and image-guidance systems such as on-board KV/MV imaging, cone-beam computed tomography (CBCT), optical surface monitoring system (OSMS) and six degree of freedom (6DoF) robotic couch.

Referring to FIGS. 5-9, the support plate 12 includes a lower surface 22 for engaging the positioning system 10 with a surface of the diagnostic/therapy device to locate the positioning system on the diagnostic/therapy device, an upper surface 24 for supporting the patient P on the support plate, and a side edge 26 extending around the support plate between the upper and lower surfaces. The support plate 12 includes a top portion 28, a middle portion 30, and a bottom portion 32. The top portion 28 is configured to support the head of the patient P, the middle portion 30 is configured to support the neck, shoulders, arms and torso of the patient, and the bottom portion 32 is configured to support the lower body of the patient. The top portion 28 has a width sized to accommodate a human's head, the middle portion 30 has an increased width sized to accommodate a human's shoulders, and the bottom portion 32 has width that is smaller than the width of the middle portion but larger than the width of the top portion to accommodate a human's chest and lower body. A thickness of the bottom portion 32 tapers toward a bottom end of the support plate 12. It will be understood that the support plate 12 can have over configurations without departing from the scope of the disclosure.

A first pair of plate indexing holes 34 are located near a top of the support plate 12 in the top portion 28 and extend through the support plate from the upper surface 24 to the lower surface 22. A second pair of indexing holes 36 are located near a bottom of the support plate 12 in the bottom portion 32 and extend through the support plate from the upper surface 24 to the lower surface 22. A first channel 38 is formed in the lower surface 22 of the support plate 12 and extends transversely across the support plate. The first channel 38 is aligned with the first pair of indexing holes 34 such that the holes open into the first channel. A second channel 40 is formed in the lower surface 22 of the support plate 12 and extends transversely across the support plate. The second channel 40 is aligned with the second pair of indexing holes 36 such that the holes open into the second channel. The indexing holes 34, 36 and channels 38, 40 are configured to receive locating structure of the diagnostic/ therapy device to fixedly secure the support plate 12 in place on the device. Therefore, the positioning system 10 facilitates being placed in the same position each time it is located on the diagnostic/therapy device.

A plurality of headrest holes 42 are formed in the upper surface 24 of the support plate 12. The headrest holes 42 are configured to receive a portion of the headrest 18 to mount the headrest to the support plate 12. A plurality of bladder holes 44A-E are formed in the upper surface 24 of the support plate 12 generally between the headrest holes 42. The bladders holes 44A-E are configured to receive respective bladders 20A-E of the headrest assembly 14 for mounting the bladders to the support plate 12. The bladder holes 44A-E are centered about a longitudinal axis LA of the support plate and are spaced apart from each other along the longitudinal axis. In the illustrated embodiment, the bladder holes 44A-E have a rectangular shape however any shape of bladder hole is envisioned. The bladder holes 44A extend to an intermediate point along a thickness of the support plate forming a floor and side walls extending upward from the floor. The rectangular nature of the balder holes 44A-E produces four side walls. Recesses 46A-E are formed in three of the four side walls. A fourth side wall in each of the bladder holes 44A-E defines an output opening 48A-E that communicates with a dedicated passage 50A-E extending through the support plate 12. Each passage 50A-E extends from a respective output opening 48A-E to a respective inlet opening 52A-E formed in the side edge 26 of the bottom portion 32 of the support plate 12. As will be discussed in further detail below, the passages 50A-E provide an internal air pathway for delivering air pressure to the headrest assembly 14 to adjust the position of the patient's head and neck area. A plurality of frame holes 54 are formed in the top portion 28 of the support plate 12 and are configured to receive a portion of the head frame assembly 16 to mount the head frame assembly to the support plate.

The support plate 12 may be formed from a material that does not unduly attenuate radiation delivery. Additionally, the support plate 12 may have a configuration and material composition suitable to support the weight of a human patient.

Referring to FIGS. 1 and 10-13, the headrest assembly 14 includes the headrest 18 and bladders 20, and is configured to support a head, neck, and shoulder area of the patient P. The headrest 18 includes a top section 56, a middle section 58, and a bottom section 60. The top section 56 is configured to support a patient's head, the middle section 58 is configured to support the patient's neck, and the bottom section 60 is configured to support the patient's lower neck and upper T-spine. The headrest 18 comprises an elongate frame member defining a series of holes 62A-E spaced apart along a length of the frame member. Posts 64 extend from a bottom of the frame member and are configured for receipt in the headrest holes 42 in the support plate 12 to mount the headrest 18 to the support plate. In the illustrated embodiment, the middle section 58 has a narrowed width as compared to the top section 56 and bottom section 60. The smaller width of the middle section 58 aligned with the generally smaller width dimension of the patient's neck as compared to their head. Similarly, the width the bottom section 60 increases from the width of the middle section to accommodate the patient's upper shoulders. This design has been found to beneficially minimize the deformation of the lateral neck soft tissue where lymphatic channels pass through.

A first portion of the top section 56 has a generally horizontal support surface. A second portion of the top section 56 curves upward along a concave arc from the first portion and extends to the middle section 58 of the headrest 18 defining a curved support surface. The top section 56 defines a single hole 62A configured to receive at least a portion of a first bladder 20A to support the head.

The middle section 58 of the headrest 18 includes a first portion that curves upward along a concave arc and extends away from the top section 56 to a second portion of the middle section defining a curved support surface. The second portion of the middle section 58 has a generally horizontal support surface and extends from the first portion to a third portion of the middle section. The third portion of the middle section 58 curves downward along a concave arc and extends away from the second portion of the middle section to the bottom section 60 defining a curved support surface. The middle section 58 defines three holes 62B, 62C, 62D configured to receive a second, third, and fourth bladder 20B, 20C, 20D, respectively. The second bladder 20B is at least partially received in the hole 62B in the first portion of the middle section 58, the third bladder 20C is at least partially received in the hole 62C in the second portion of the middle section, and the fourth bladder 20D is at least partially received in hole 62D in the third portion of the middle section.

The bottom section 60 of the headrest 18 extends from the third portion of the middle section 58 to a bottom end of the headrest. The bottom section 60 curves downward from the third portion of the middle section 58 along a concave arc that is continuous with the concave arc of the third portion of the middle section defining a curved support surface. The bottom section 60 defines a single hole 62E configured to receive at least a portion of a fifth bladder 20E. The headrest 18 may be formed from any suitable radiolucent material. In a preferred embodiment, the material of the headrest 18 reduces the attenuation of a radiation beam and minimizes any bolus effect (beam entrance skin dose in contact with the headrest).

Referring to FIGS. 14-18B, the bladders 20A-E are received in respective bladder holes 44A-E in the support plate 12 and aligned with the respective holes 62A-E in the headrest 18 to mount the bladders to the support plate. The first bladder 20A (FIGS. 15A and 15B) has a generally cuboidal shape including four sides 66A, a horizontal top surface 68A, and a bottom surface 70A. Three of the four sides 66A each have a projection 72A extending from a bottom portion of the bladder 20A. In the illustrated embodiment, the projections 72A are cylindrical. However, the projections could have any shape without departing from the scope of the disclosure. A fourth side 66A of the first bladder 20A has a port 74A extending therefrom and in fluid communication with an interior of the first bladder. The projections 72A are configured to be received in the recesses 46A in the first bladder hole 44A to secure the first bladder 20A in the first bladder hole. The port 74A is received in the output opening 48A in the first bladder hole 44A for placing the port in fluid communication with a first passage 50A in the support plate 12. The first bladder 20A is configured to receive air delivered through the first passage 50A for inflating the first bladder to adjust a head position of the patient P. As such, directing air pressure into the bladder 20A will cause the top surface 68A to rise thereby lifting the patient's head, and reducing air pressure from the bladder will cause the top surface to drop thereby lowering the patient's head. It will be understood that the first bladder 20A could have other shapes and configurations without departing from the scope of the disclosure.

Figure 16A:
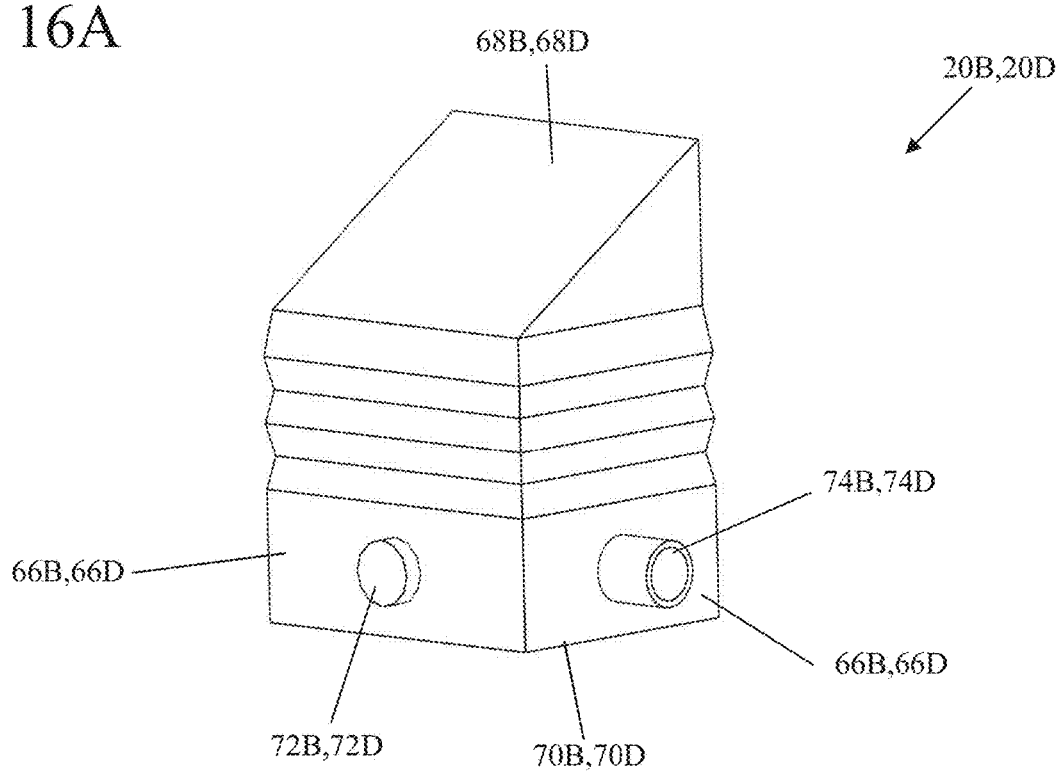
FIGS. 16A and 16B are perspective views of a second and fourth bladder.
Figure 16B:
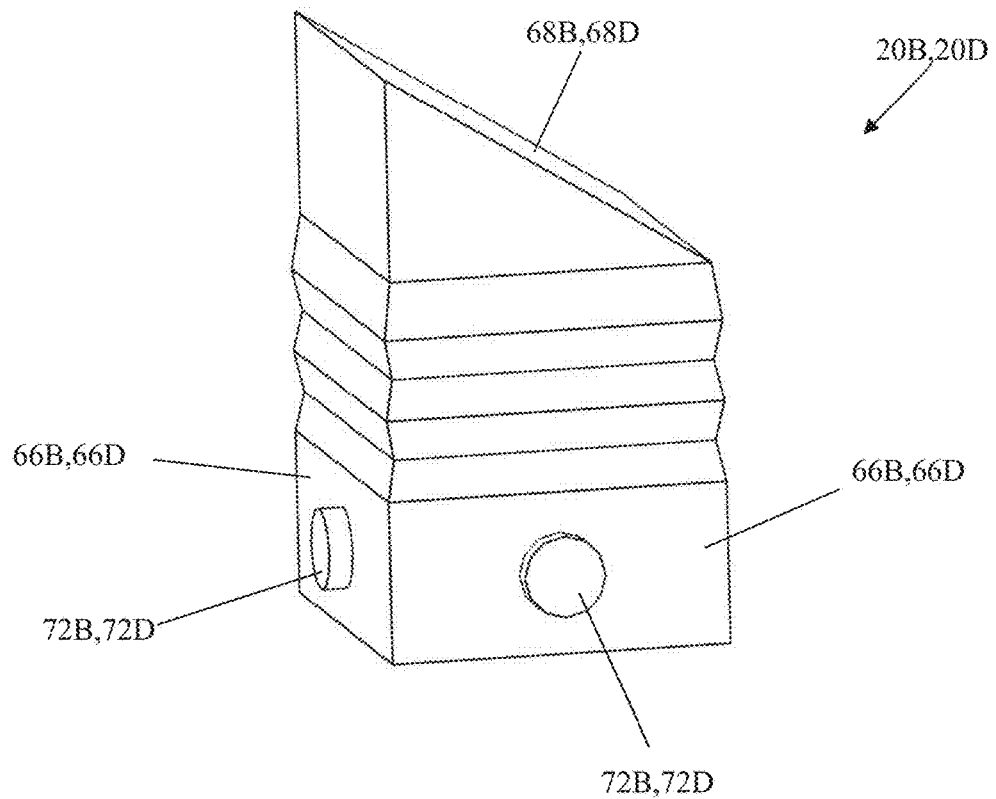

Referring to FIGS. 16A and 16B, the second bladder 20B has a generally trapezoidal shape including four sides 66B, an angled top surface 68B, and a bottom surface 70B. Three of the four sides 66B each have a projection 72B extending from a bottom portion of the bladder 20B. In the illustrated embodiment, the projections 72B are cylindrical. However, the projections could have any shape without departing from the scope of the disclosure. A fourth side 66B of the second bladder 20B has a port 74B extending therefrom and in fluid communication with an interior of the second bladder. The projections 72B are configured to be received in the recesses 46B in the second bladder hole 44B to secure the second bladder 20B in the second bladder hole. The port 74B is received in the output opening 48B in the second bladder hole 44B for placing the port in fluid communication with a second passage 50B in the support plate 12. The second bladder 20B is configured to receive air delivered through the second passage 50B for inflating the second bladder to adjust an upper C-spine position of the patient P. As such, directing air pressure into the bladder 20B will cause the angled top surface 68B to rise thereby lifting the patient's upper neck, and reducing air pressure from the bladder will cause the angled top surface to drop thereby lowering the patient's upper neck. It will be understood that the second bladder 20B could have other shapes and configurations without departing from the scope of the disclosure.

Figure 17A:
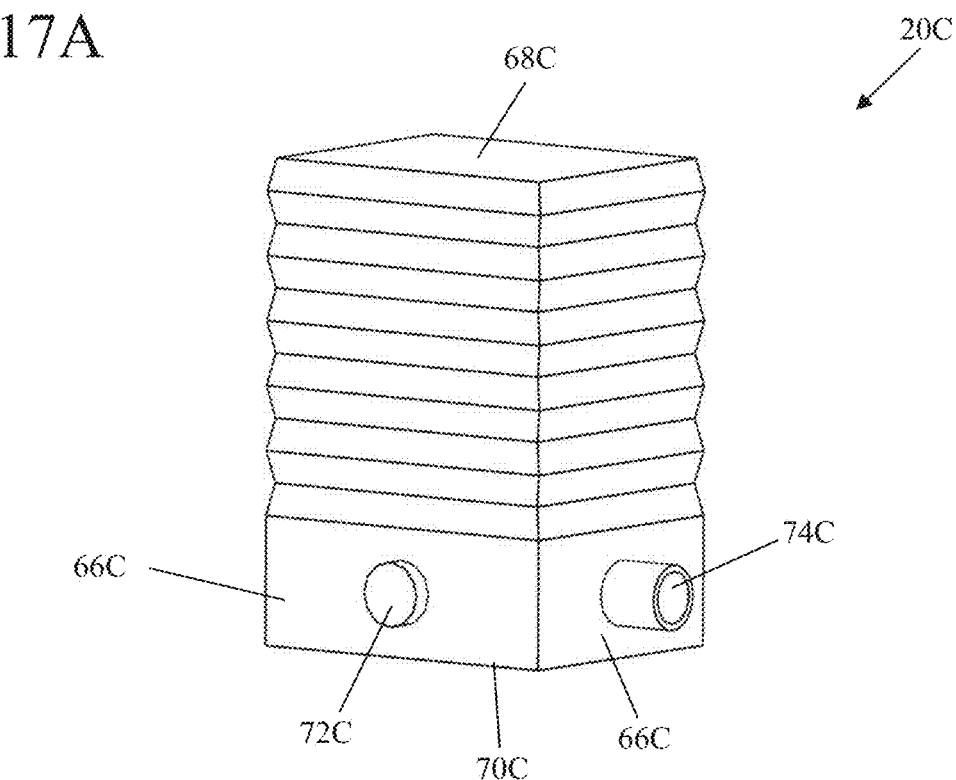
FIGS. 17A and 17B are perspective views of a third bladder.
Figure 17B:
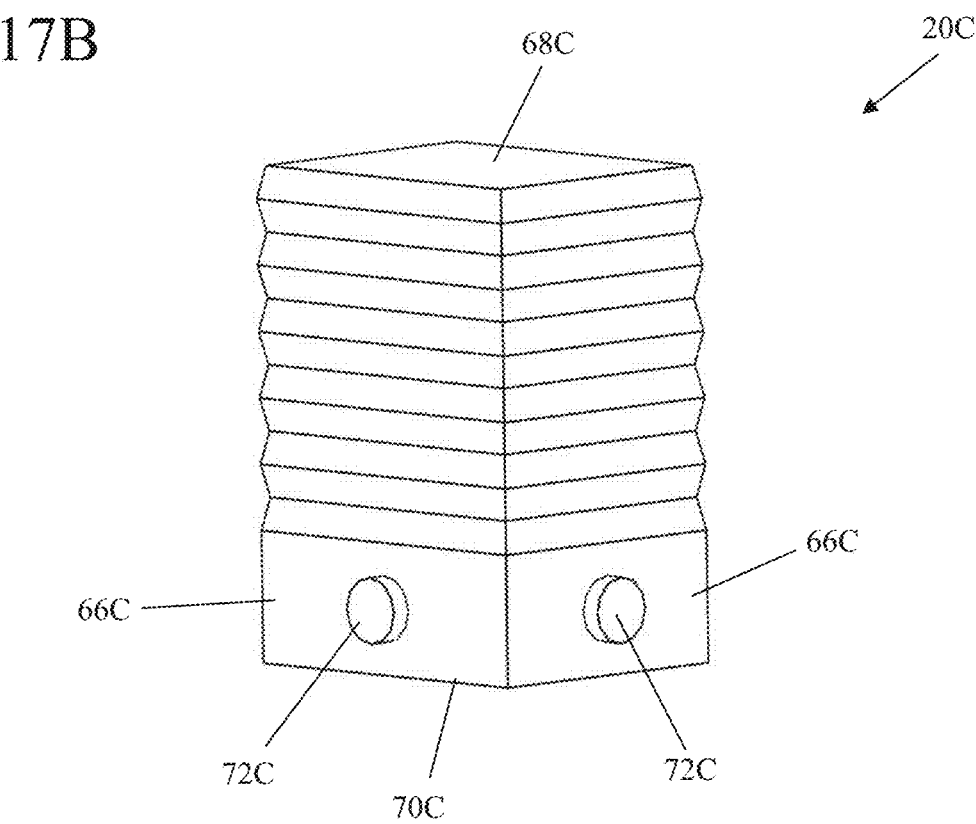

Referring to FIGS. 17A and 17B, the third bladder 20C has a generally cuboidal shape including four sides 66C, a horizontal top surface 68C, and a bottom surface 70C. Three of the four sides 66C each have a projection 72C extending from a bottom portion of the bladder 20C. In the illustrated embodiment, the projections 72C are cylindrical. However, the projections could have any shape without departing from the scope of the disclosure. A fourth side 66C of the third bladder 20 C has a port 74C extending therefrom and in fluid communication with an interior of the third bladder. The projections 72C are configured to be received in the recesses 46C in the third bladder hole 44C to secure the third bladder 20C in the third bladder hole. The port 74C is received in the output opening 48C in the third bladder hole 44C for placing the port in fluid communication with a third passage 50C in the support plate 12. The third bladder 20C is configured to receive air delivered through the third passage 50C for inflating the third bladder to adjust a middle C-spine position of the patient P. As such, directing air pressure into the bladder 20C will cause the horizontal top surface 68C to rise thereby lifting the patient's middle neck, and reducing air pressure from the bladder will cause the horizontal top surface to drop thereby lowering the patient's middle neck. It will be understood that the third bladder 20C could have other shapes and configurations without departing from the scope of the disclosure.

Referring to FIGS. 16A and 16B, the fourth bladder 20D has a generally trapezoidal shape including four sides 66D, an angled top surface 68D, and a bottom surface 70D. Three of the four sides 66D each have a projection 72D extending from a bottom portion of the bladder 20D. In the illustrated embodiment, the projections 72D are cylindrical. However, the projections could have any shape without departing from the scope of the disclosure. A fourth side 66D of the fourth bladder 20D has a port 74D extending therefrom and in fluid communication with an interior of the fourth bladder. The projections 72D are configured to be received in the recesses 46D in the fourth bladder hole 44D to secure the fourth bladder 20D in the fourth bladder hole. The port 74D is received in the output opening 48D in the fourth bladder hole 44D for placing the port in fluid communication with a fourth passage 50D in the support plate 12. The fourth bladder 20D is configured to receive air delivered through the fourth passage 50D for inflating the fourth bladder to adjust a lower C-spine position of the patient P. As such, directing air pressure into the bladder 20D will cause the angled top surface 68D to rise thereby lifting the patient's lower neck, and reducing air pressure from the bladder will cause the angled top surface to drop thereby lowering the patient's lower neck. It will be understood that the fourth bladder 20D could have other shapes and configurations without departing from the scope of the disclosure.

Figure 18A:
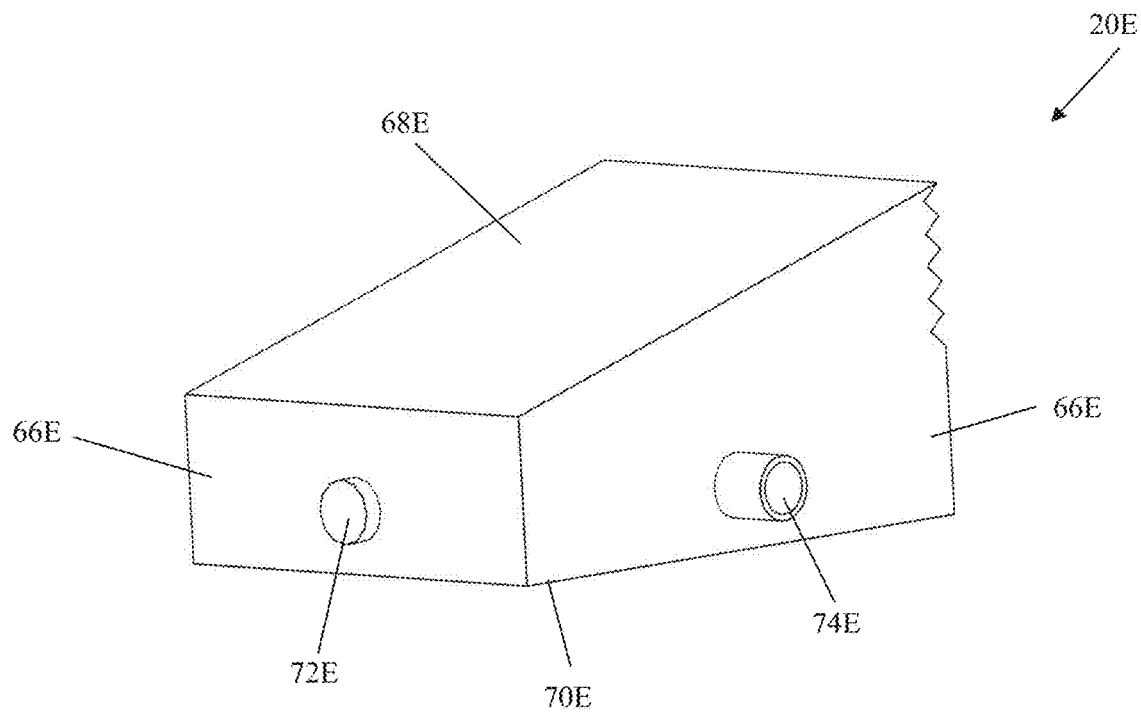
FIGS. 18A and 18B are perspective views of a fifth bladder.
Figure 18B:
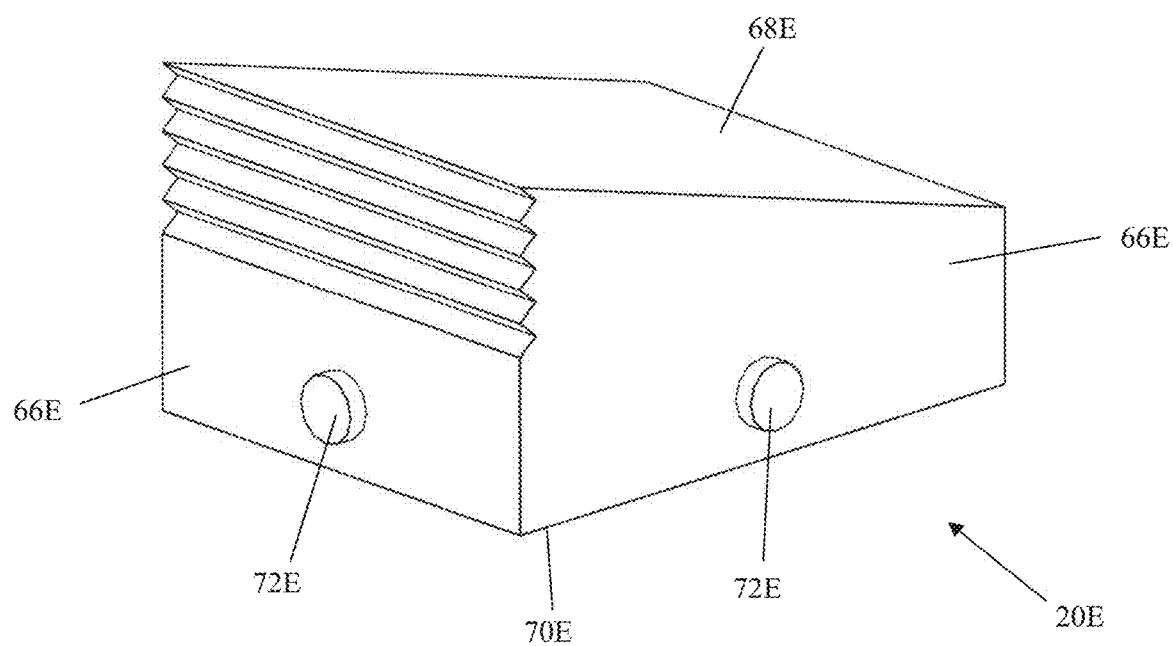

Referring to FIGS. 18A and 18B, the fifth bladder 20E has a generally trapezoidal shape including four sides 66E, an angled top surface 68E, and a bottom surface 70E. Three of the four sides 66E each have a projection 72E extending from a bottom portion of the bladder 20E. In the illustrated embodiment, the projections 72E are cylindrical. However, the projections could have any shape without departing from the scope of the disclosure. A fourth side 66E of the fifth bladder 20E has a port 74E extending therefrom and in fluid communication with an interior of the fifth bladder. The projections 66E are configured to be received in the recesses 46E in the fifth bladder hole 44E to secure the fifth bladder 20E in the fifth bladder hole. The port 74E is received in the output opening 48E in the fifth bladder hole 4E for placing the port in fluid communication with a fifth passage 50E in the support plate 12. The fifth bladder 20E is configured to receive air delivered through the fifth passage 50E for inflating the fifth bladder to adjust an upper T-spine position of the patient P. As such, directing air pressure into the bladder 20E will cause the angled top surface 68E to rise thereby lifting the patient's upper T spine and lower C-spine, and reducing air pressure from the bladder will cause the angled top surface to drop thereby lowering the patient's upper T-spine and lower C-spine. It will be understood that the fifth bladder 20E could have other shapes and configurations without departing from the scope of the disclosure.

Additionally or alternatively, each bladder 20A-E may include multiple chambers that are collectively and/or separately inflatable. For instance, one or more of the bladders 20A-E may have left and right chambers for selectively adjusting a left or right side of the patient's anatomy such as to produce a desired roll of the patient's anatomy. Similarly, top or bottom chambers may be arranged within one or more bladders 20A-E for adjusting an anterior or posterior positioning of the patient's anatomy. In one embodiment, two chambers/bladders can control roll of the patient's head, one chamber/bladder can provide anterior/posterior adjustment to the back of the skull, three chambers/bladders can be arranged to adjust the curvature of the cervical vertebrae, two chambers/bladders can provide for anterior/posterior adjustment of the lower spine and upper thoracic vertebrae, and two chambers/bladders can control the positioning of the patient's shoulders. Valves (not shown) may be disposed along the fluid path for selectively directing air into a particular bladder or chamber within a bladder. Still other numbers and arrangements of bladders and chambers within the bladders is envisioned.

Figure 19A:
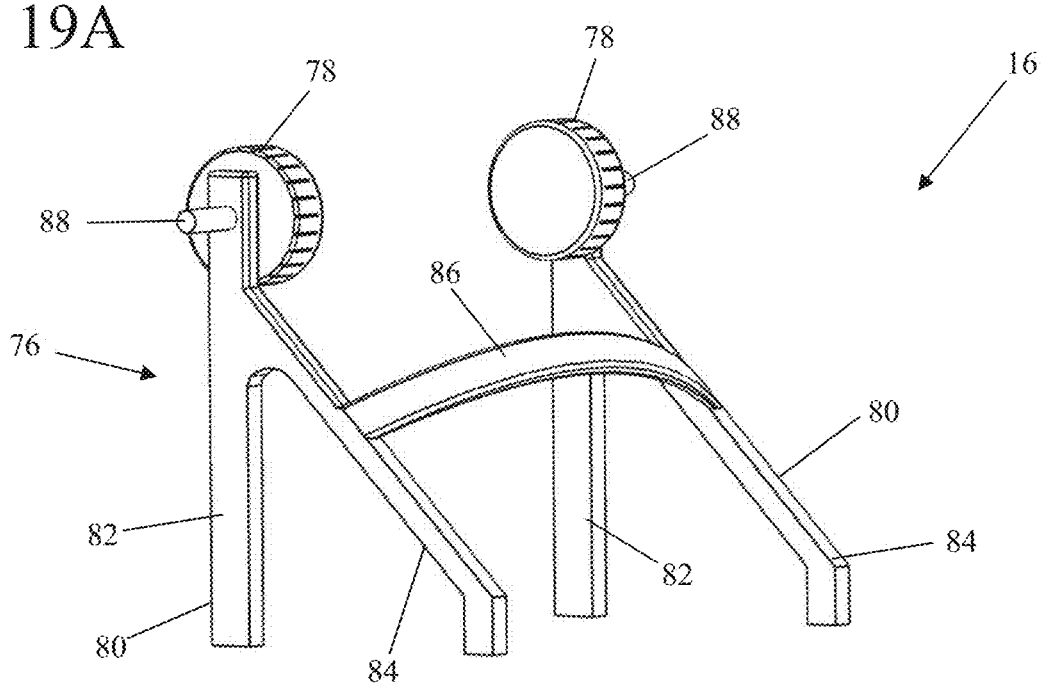
FIGS. 19A and 19B are perspective views of a head frame assembly of the patient positioning system.
Figure 19B:
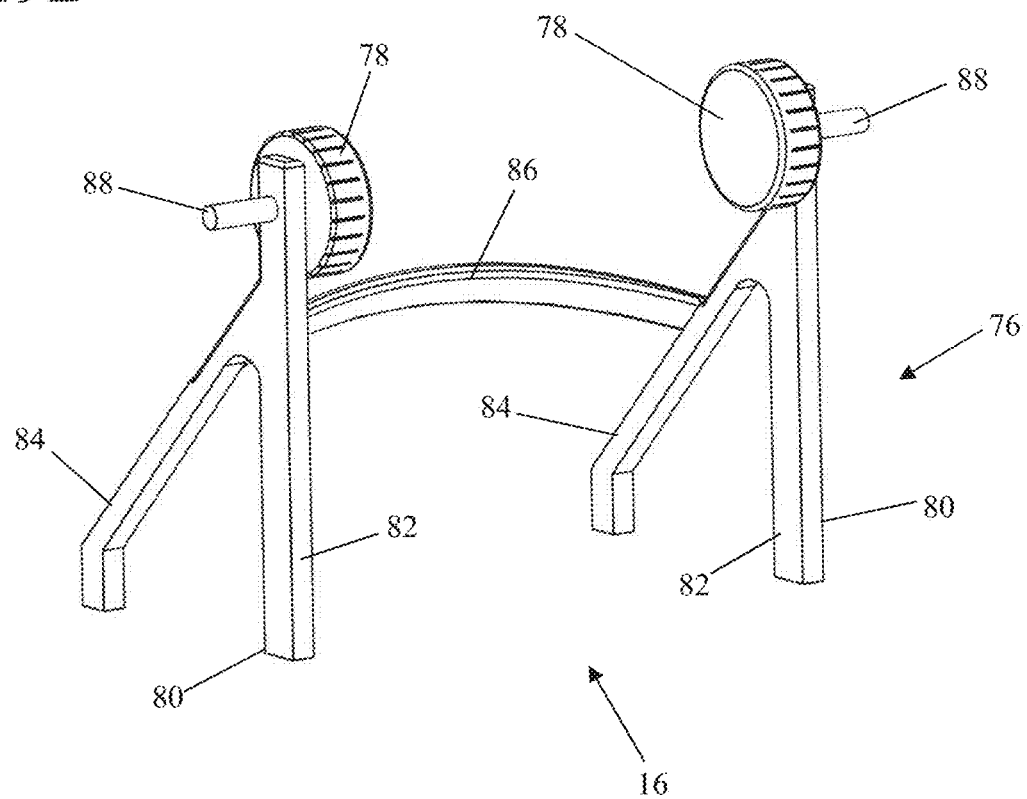

Referring to FIGS. 19A and 19B, the head frame assembly 16 includes a head frame 76 and a pair of adjustable pads 78 movably mounted on the head frame for opposing opposite sides of the patient's head to locate the patient's head in place on the support plate 12. The frame 76 includes a pair of frame members 80 each comprising a first arm 82 and a second arm 84 extending rearwardly from the first arm. A frame bar 86 extends between the second arms 84 of the frame members 80. The frame bar 86 is curved to generally accommodate the shape of the patient's head. Bottom ends of the first and second arms 82, 84 of the frame 76 are received in respective frame holes 54 for securing the frame to the support plate 12. A threaded rod 88 extends from each pad 78 and is received within a respective threaded hole in a first arm 82 of one the frame members 80. Thus, rotating the pads 78 will cause translational movement of the pads toward and away from a center of the frame 76 to adjust for the size and orientation of the patient's head. It will be understood that while the head frame assembly 16 can restrict the head of the patient P from lateral roll, some degree of lateral roll movement of the head and movement of the head in the anteroposterior direction is still permitted. In one embodiment, the pads 78 are formed from a hollow radiolucent plastic material. However, any suitable material may be used.

Figure 20:
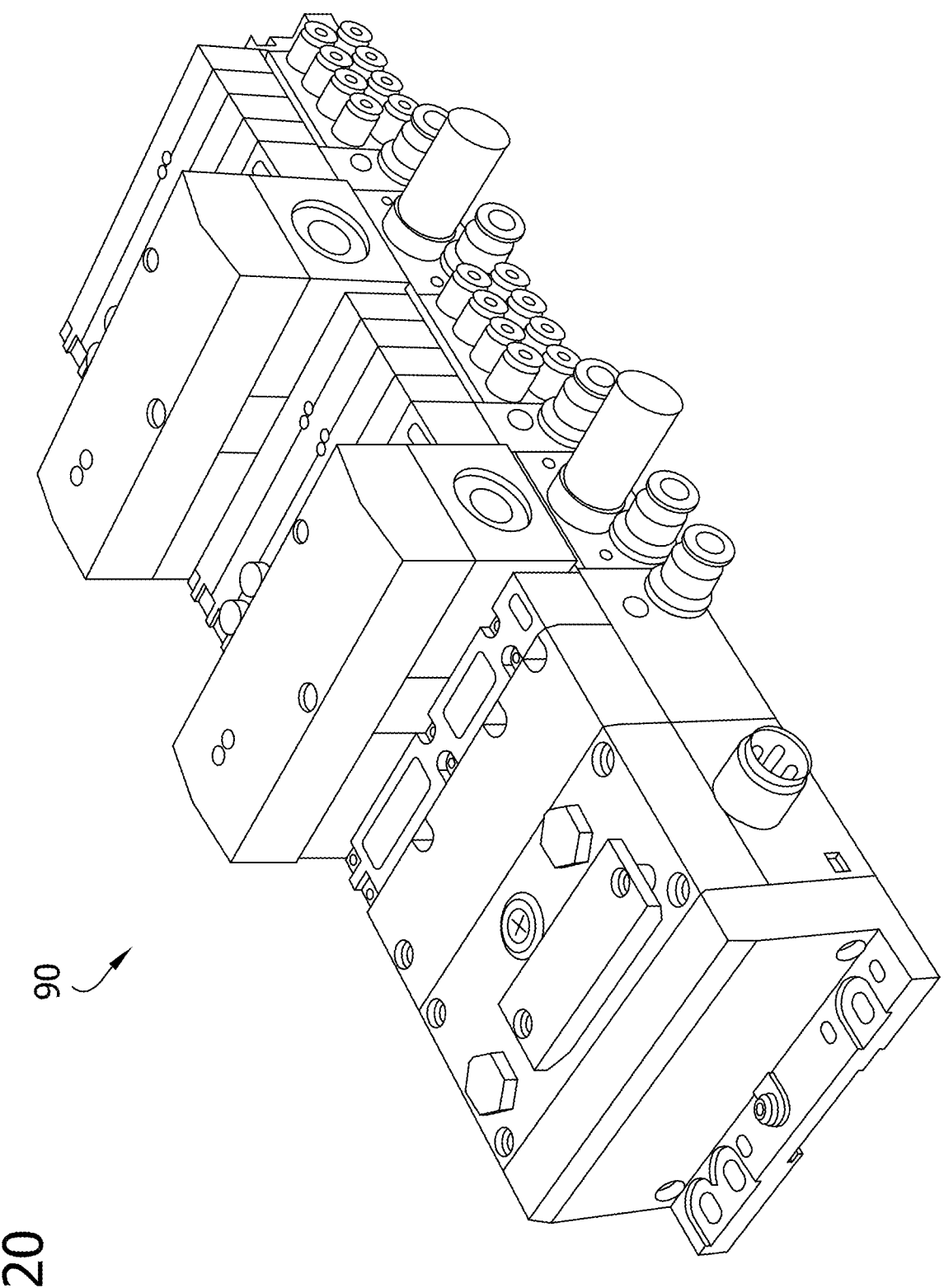
FIG. 20 is a perspective of a controller of the patient positioning system.
Figure 21:
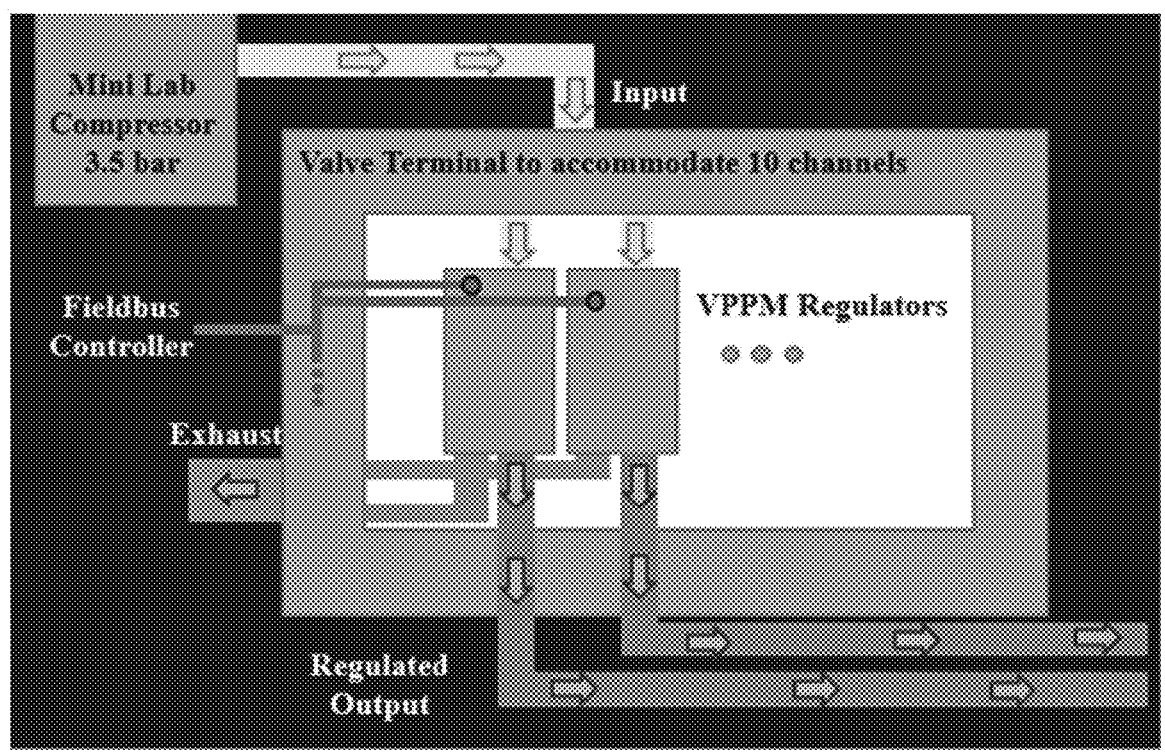
FIG. 21 is a schematic illustration of a control system.

The patient positioning system 10 can be connected to a pneumatic controller 90 (FIG. 20) for supplying pressurized air to the bladders 20A-E. Tubing (not shown) may extend from the controller to the input openings 52A-D in the support plate 12 for placing the bladders 20A-E in fluid communication with the source of pressurized air. The controller and other relevant electronics can be positioned near the base of the treatment table outside of the primary area of radiation. A schematic illustration of the control system is shown in FIG. 21. By electronically adjusting the set-points of pressure regulators of the controller, the pressure within each bladder will increase or decrease accordingly resulting in physical displacement of the patient resting on the bladders 20A-E.

In use, an operator can compare a real-time x-ray image of the patient P to a reference image produced from a reference CT simulation and/or digitally reconstructed radiograph (DRR). Then the operator can adjust the headrest assembly 14 of the patient positioning system 10 such that the patient would be positioned to minimize the difference between any real-time or subsequent real-time x-ray images and the reference image. The reference image can be generated from a treatment planning system. The x-ray images are generated in real-time such as on a radiation therapy machine. The final position can be based on an operator interpretation of the match based on the patient's bony anatomy. Accordingly, the patient positioning system 10 can be used to reliably reproduce patient positioning for matching reference images to apply repeated treatment to a desired area.

Alternatively, the matching process can be automated. For example, image processing can be used to detect the bone edges on all images, quantification of the displacement 2D vector can be calculated, and a machine learning predictive model can control the pneumatic system and adjust the position of the patient by automatically inflating and deflating the bladders 20A-E with a minimum number of iterations.

Referring to FIGS. 22-29B, 37, and 38 a patient positioning system of another embodiment is generally indicated at 100. The system 100 is substantially similar to system 10 and thus like elements have been given like reference numbers plus 100. The system 100 includes a support plate 112 for supporting a patient P in a diagnostic/therapy device, a headrest assembly 114 for supporting and adjusting a position of the patient's head and neck area on the support plate, and a head frame assembly 116 mounted on the support plate for providing a positioning reference for the patient's head. The headrest assembly 114 comprises a headrest 118 (FIG. 25) and a plurality of inflatable bladders 120 (FIGS. 29A and 29B) and is configured to adjust the position of the patient's head, spine flexure (e.g., cervical vertebrae), and supraclavicular positions as was previously described for headrest assembly 14. In the illustrated embodiment, the system 100 is configured as a maskless positioning system such that a mask covering the patient's face is not utilized to position the patient. However, a mask could be used without departing from the scope of the disclosure.

Figure 22:
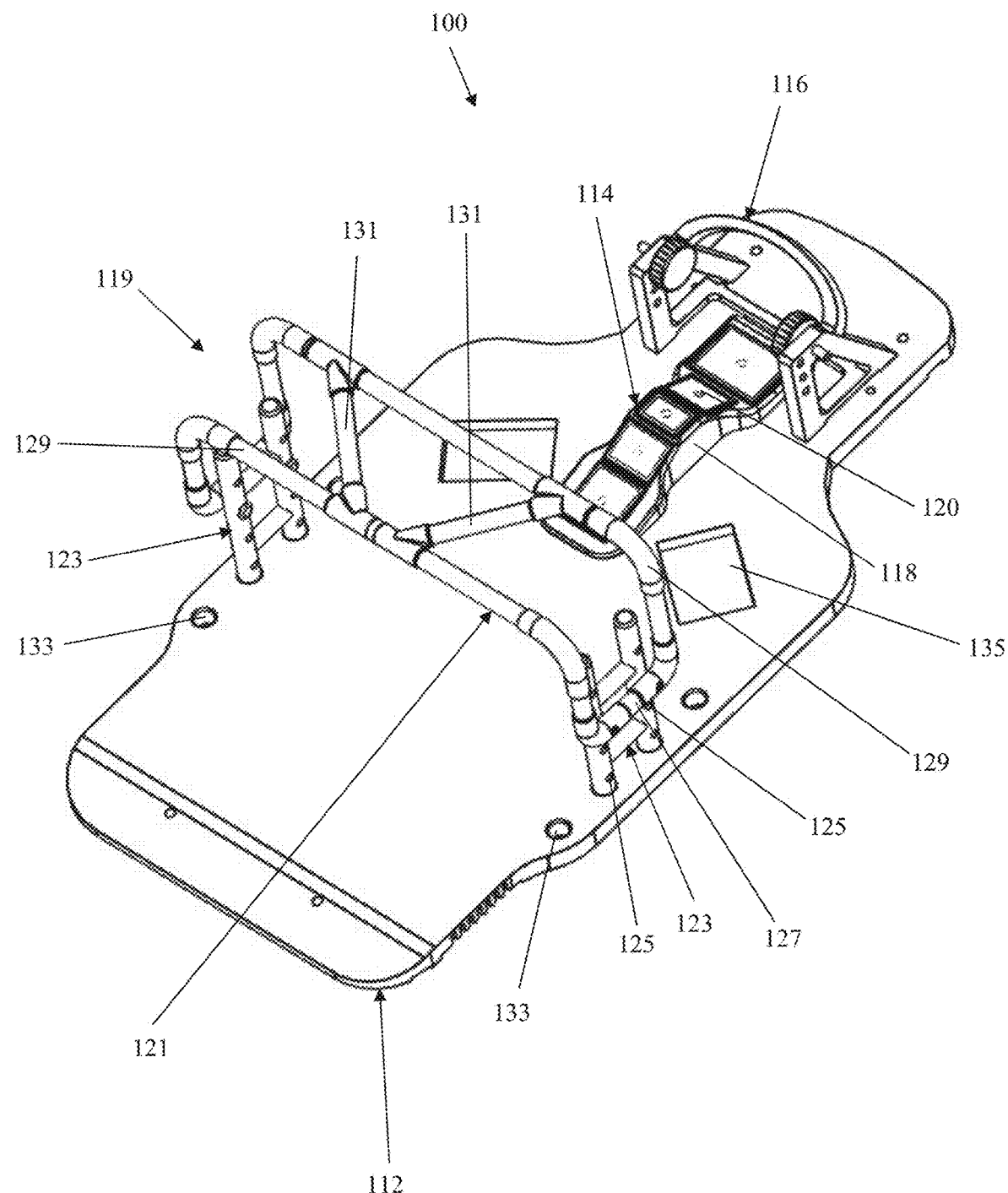
FIG. 22 is a perspective view of a patient positioning system of another embodiment.

Referring to FIG. 22, the system 100 includes a handle assembly 119 configured to assist the patient P in properly locating themselves on the support plate 112. In particular, the patient P can grasp the handle assembly 119 with their arms close to their sides (i.e., next to their torso) and bent at the elbows such that their forearms extend generally vertically. This will generally locate the patient's upper body on the headrest assembly 114 in a proper and reproducible position for daily treatments. The handle assembly 119 includes a crossbar 121 extending laterally across a width of the support plate 112, and a pair of attachment members 123 attached to ends the crossbar and securing the crossbar to the support plate. The location at which the crossbar 121 is attached to the attachment members 123 can be adjusted to adjust a height of the crossbar above the support plate 112. Fastener holes 125 in the attachment member 123 are vertically spaced and configured to receive fasteners (not shown) extending through aligned fastener holes 127 in the crossbar 121 to attach the crossbar to the attachment members at different locations. In the illustrated embodiment, the crossbar 121 is generally U-shaped including a pair of cross members 129 and connecting arms 131 extending between the cross members. The cross members 129 provide structure for the patient P to grasp the crossbar 121, and the connecting arms 131 may provide structural rigidity to the crossbar. However, the crossbar 121 could have over configurations without departing from the scope of the disclosure.

Figure 23:
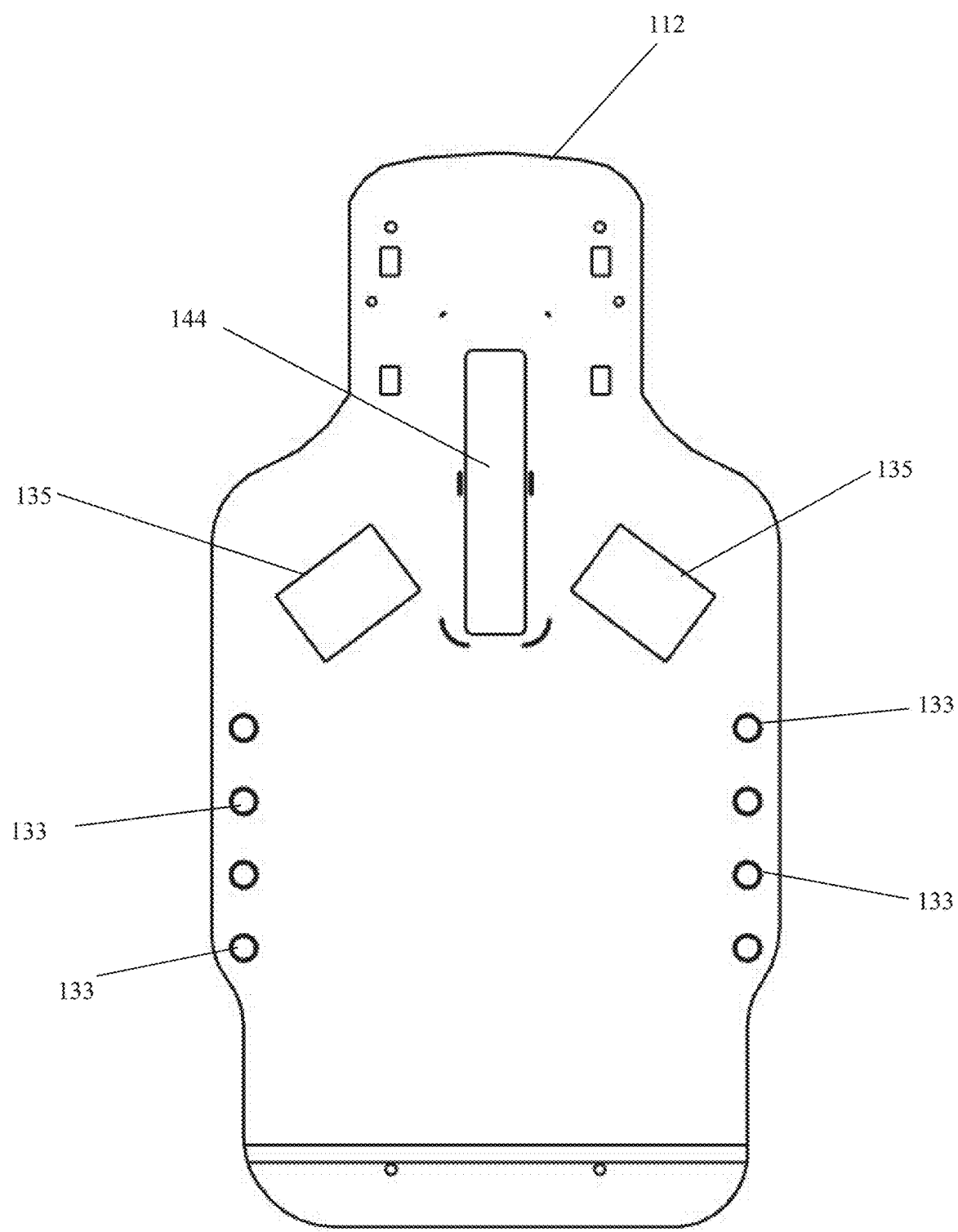
FIG. 23 is a top plan view of a support plate of the patient positioning system in FIG. 22.

Referring to FIGS. 22 and 23, attachment member holes 133 in a middle portion of the support plate 112 receive ends of the attachment member 123 to mount the handle assembly 119 on the support plate. A plurality of attachment member holes 133 are spaced longitudinally along the support plate 112 so that the longitudinal position of the handle assembly 119 can be adjusted to accommodate the torso length of the patient P. The handle assembly 119, however, could be mounted on the support plate by other means without departing from the scope of the disclosure.

Figure 24:
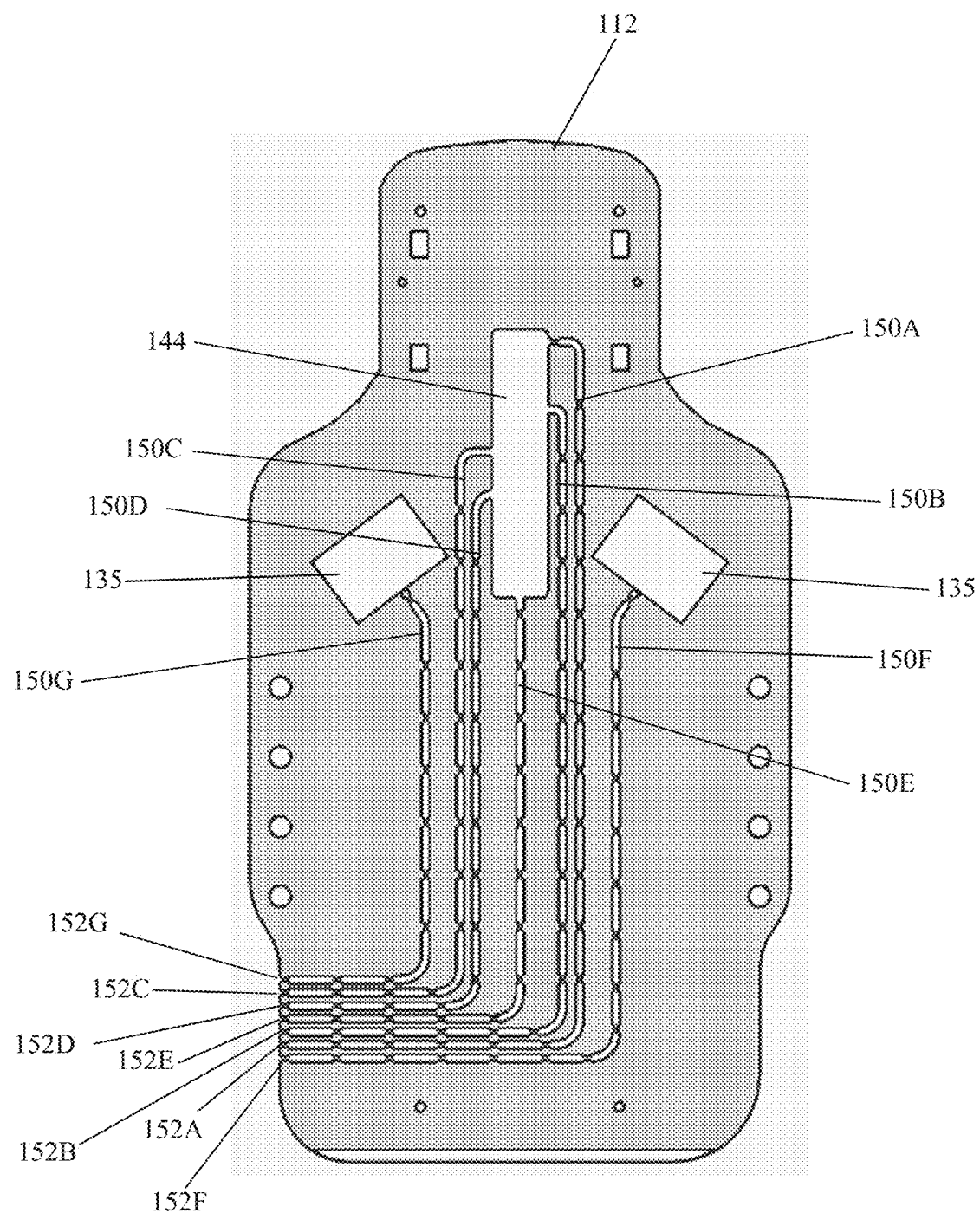
FIG. 24 is a section of the support plate in FIG. 23.
Figure 25:
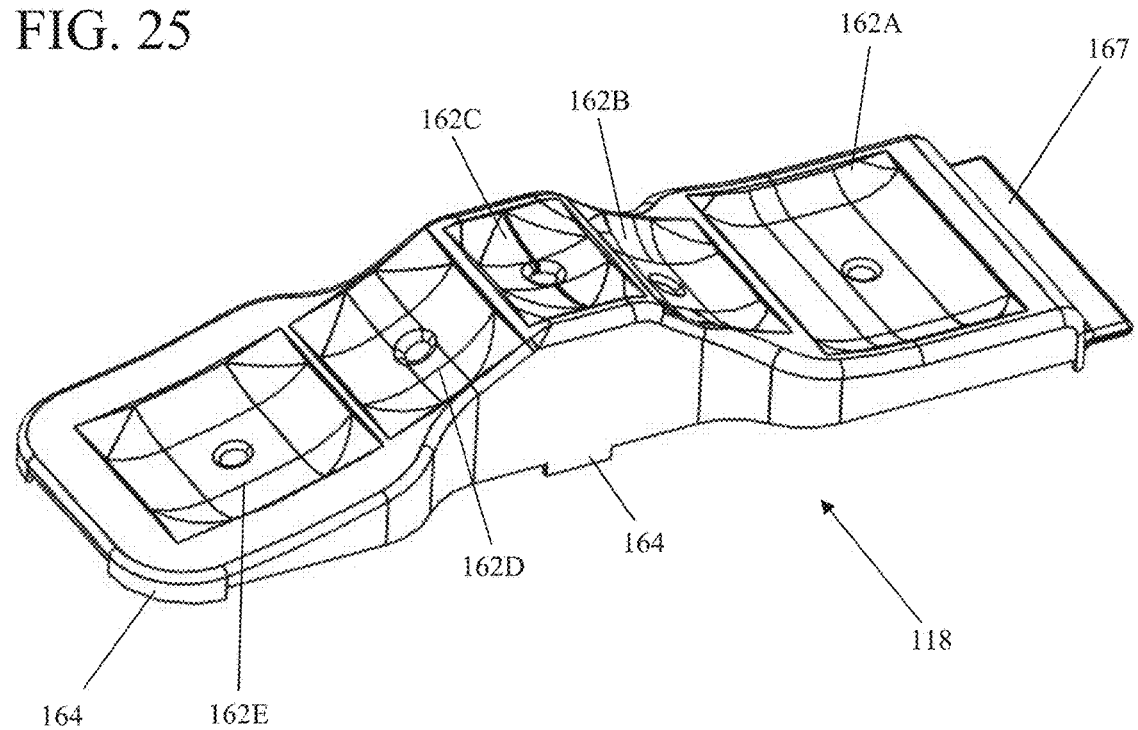
FIG. 25 is a perspective of a headrest of the patient positioning system in FIG. 22.
Figure 26:
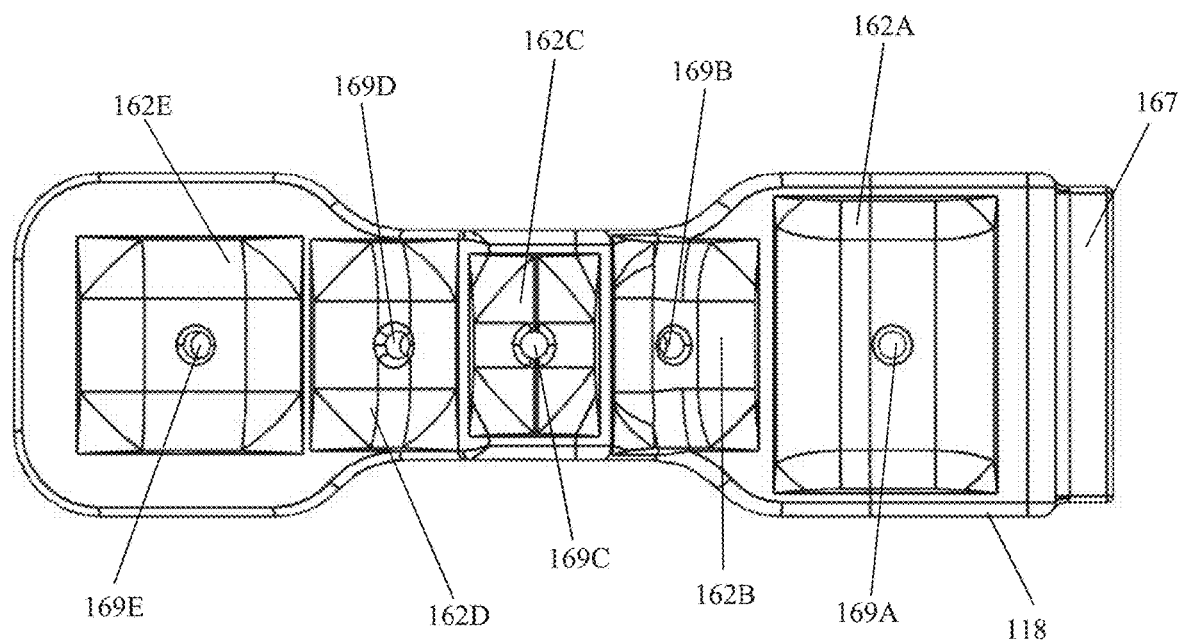
FIG. 26 is a top plan view of the headrest in FIG. 25.
Figure 27:
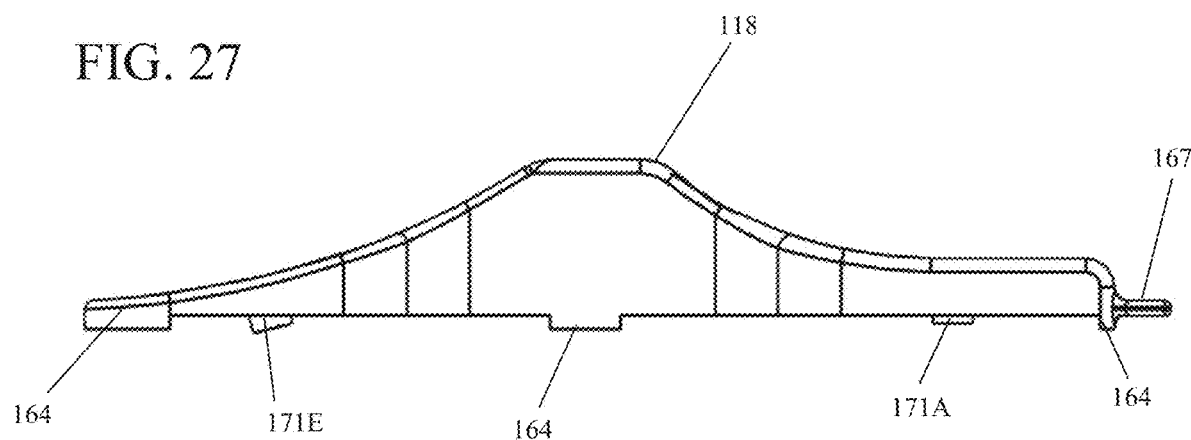
FIG. 27 is a side view of the headrest in FIG. 25.
Figure 28:
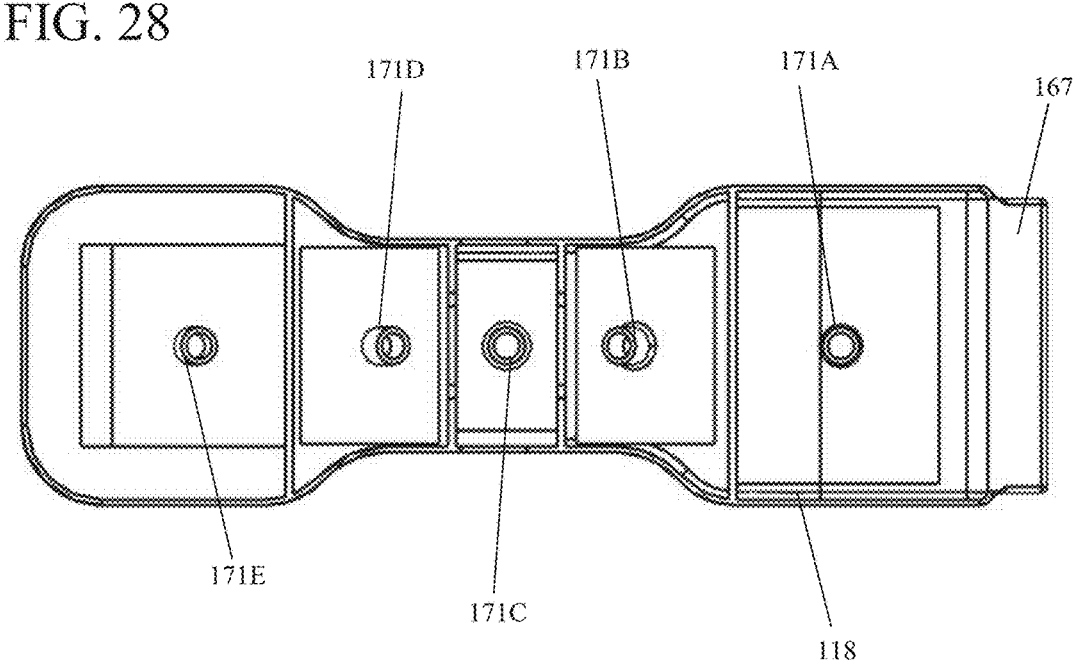
FIG. 28 is a bottom plan view of the headrest in FIG. 25.
Figure 29A:
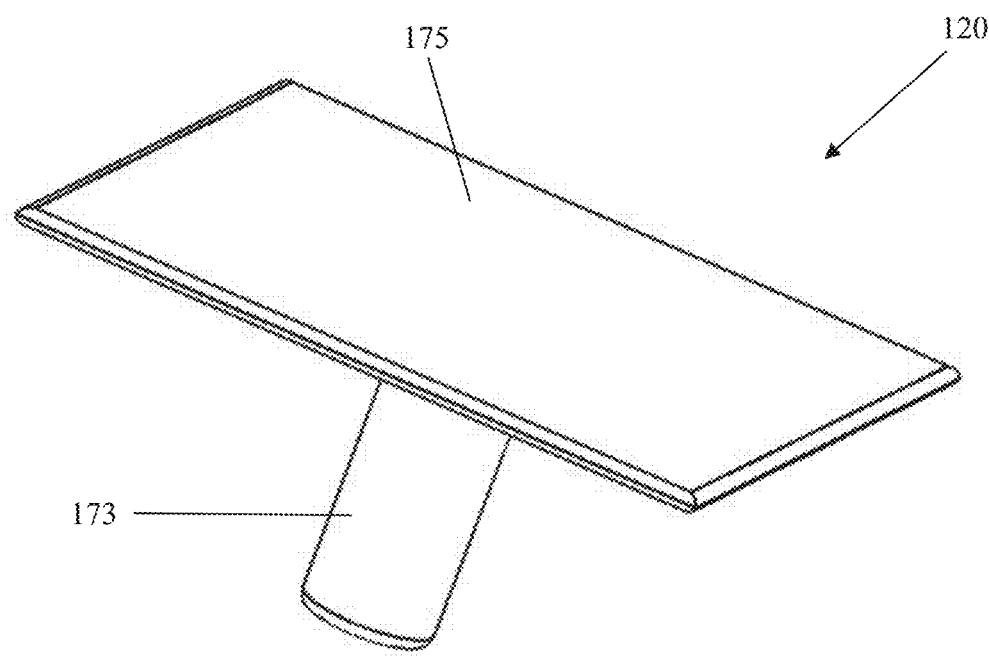
FIG. 29A is a top perspective of a bladder of the patient positioning system in FIG. 22.
Figure 29B:
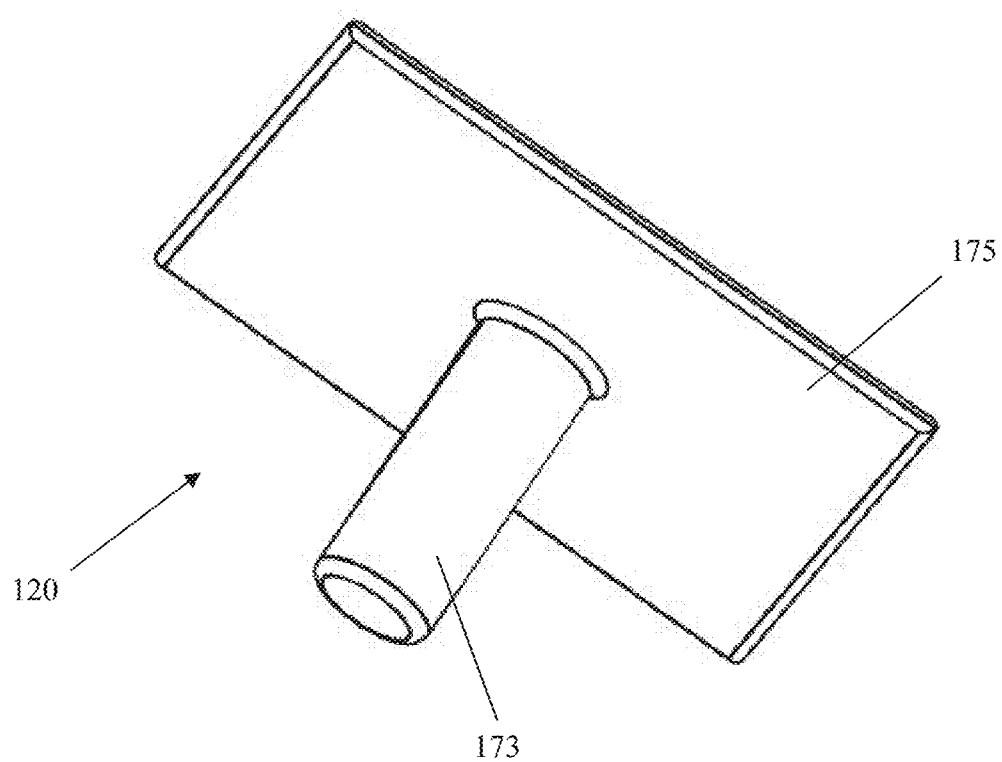
FIG. 29B is a bottom perspective of a bladder of the patient positioning system in FIG. 22.
Figure 30:
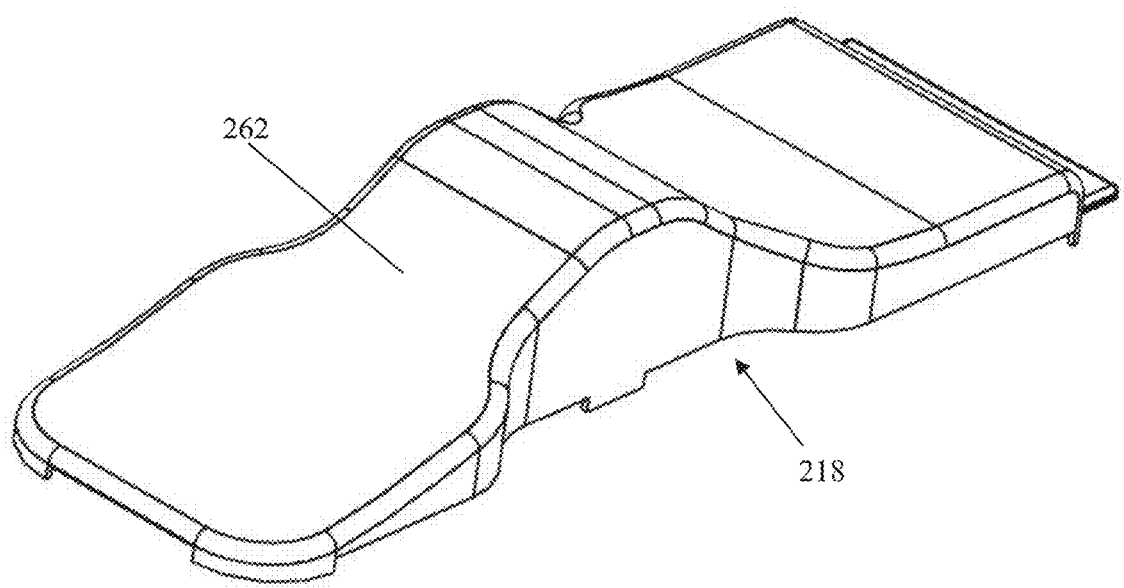
FIG. 30 is a perspective of a headrest of another embodiment.
Figure 31:
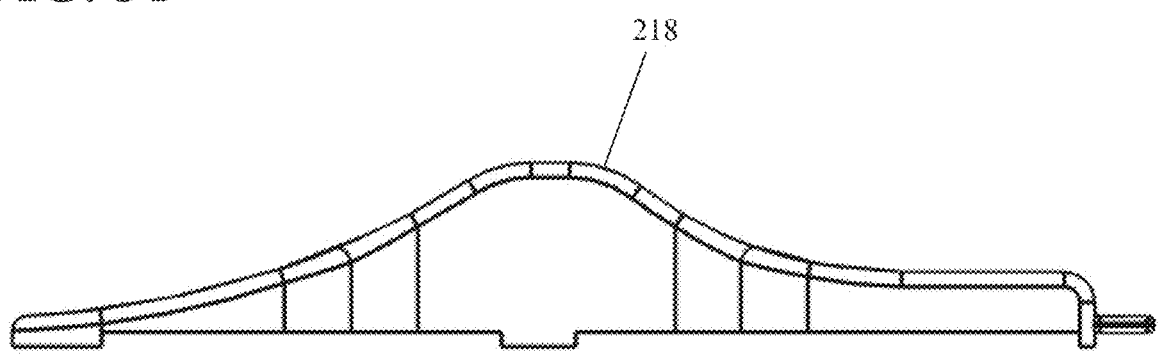
FIG. 31 is a side view of the headrest in FIG. 30.
Figure 32:
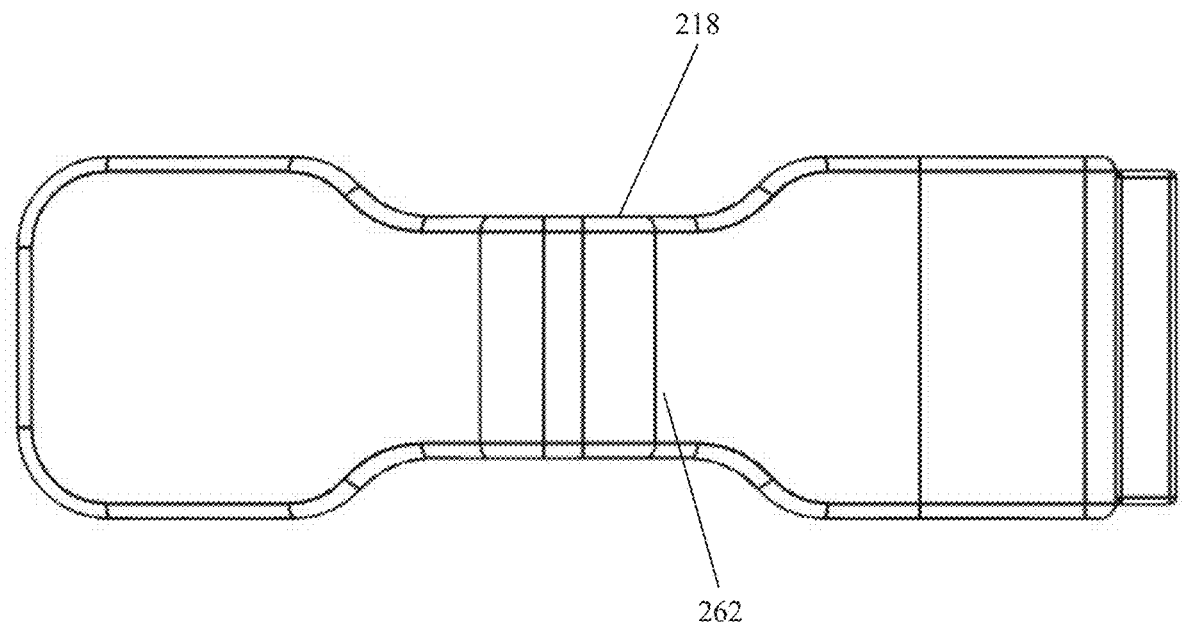
FIG. 32 is a top perspective of the headrest in FIG. 30.
Figure 33:
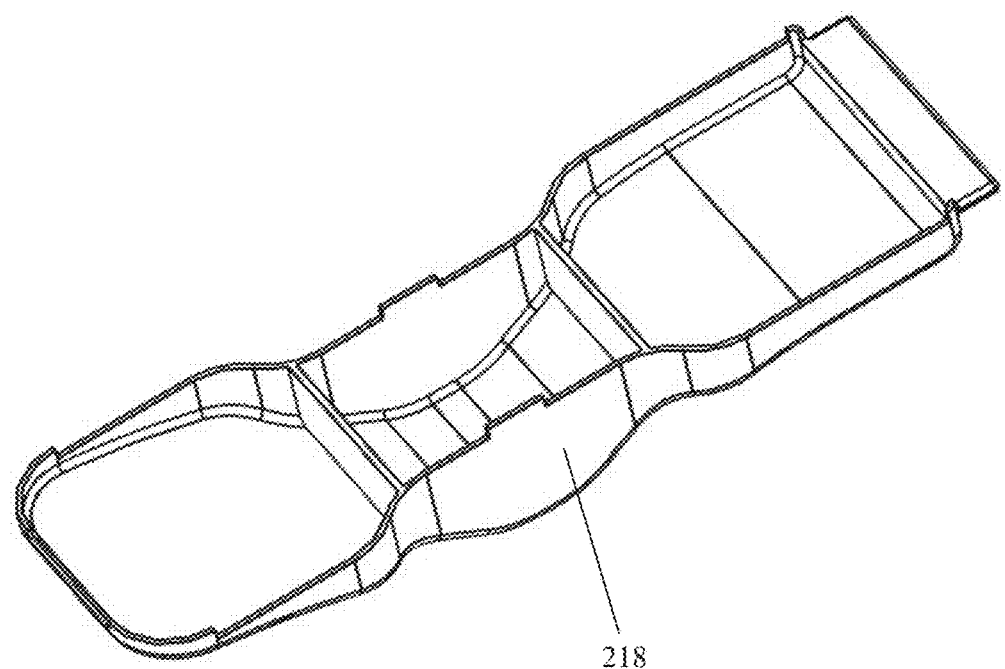
FIG. 33 is a bottom perspective of the headrest in FIG. 30.

Referring to FIGS. 23 and 24, a single bladder hole 144 is formed in the upper surface of the support plate 112. The bladder hole 144 is configured to receive bladders 120 (FIGS. 29A and 29B) of the headrest assembly 114 for locating the bladders relative to the support plate 112. The bladder hole 144 is centered about a longitudinal axis of the support plate. In the illustrated embodiment, the bladder hole 144 has a rectangular shape however any shape of bladder hole is envisioned. In the illustrated embodiment, the bladder hole 144 extends entirely through a thickness of the support plate 112. The support plate 112 also defines a pair of recesses 135 in a middle portion of the support plate. The recesses 135 are located on opposite sides of the bladder hole 144. The recesses 135 are also configured to receive an inflatable bladder 120 (FIG. 29) to support a shoulder of the patient P. Thus, the bladders 120 in the recesses 135 are configured to adjust a position of the patient's shoulders. The recesses 135 (and bladders 120 in the recesses) also provide a visual representation of where the patient P is to locate their shoulders to properly position their head and neck in the headrest assembly 114. Other methods for locating the patient's shoulders on the support plate 112 may be provided without departing from the scope of the disclosure.

Passages 150A-E communicate with the bladder hole 144 and extend from the bladder hole to respective inlet opening 152A-E formed in a side edge of a bottom portion of the support plate 112. As explained in the previous embodiment, the passages 150A-E provide an internal air pathway for delivering air pressure to the headrest assembly 114 to adjust the position of the patient's head and neck area. Additional passages 150F and 150G communicate with the recesses 135, respectively, and provide an internal air pathway for delivering air within the support plate 112 to additional inflatable bladders 120 disposed in the recesses for adjusting a position of the patient's shoulders.

Referring to FIGS. 25-28, the headrest 118 comprises a frame member including a top section, a middle section, and a bottom section. The headrest 118 is substantially similar to the headrest 18 of the previous embodiment. However, instead of holes for receiving the bladders, the headrest 118 defines a series of support surfaces 162A-E spaced apart along a length of the headrest and configured to seat one of the inflatable bladders 120. The support surfaces 162A-E have a concave shape such that the support surface and bladder 120 support the patient's bones while also allowing the lateral soft tissue where the lymphatic channels pass through to sag freely downward so that the shape of these lymphatic channels is least disturbed under the influence of the engagement of the headrest 118 with the patient's bones. However, the support surfaces 162A-E could have other shapes without departing from the scope of the disclosure. For example, the support surfaces 162A-E could be flat or convex. Alternatively, the support surfaces could have a varying profile.

The bladders 120 are supported on top of the support surfaces 162A-E and are operable to inflate and deflate to raise and lower the position the patient's head and neck as desired. A bottom surface of the bladders may also be convex or otherwise shaped to match the surface profile of the support surface 162A-E on which the bladder is located. Tabs 164 extend from a bottom of the frame member and are configured for receipt in the headrest slots in the support plate 112 to mount the headrest 118 to the support plate. A flange 167 extends from a top of the frame member and is configured to locate the headrest 118 relative to the head frame assembly 116.

A top section of the headrest 118 defines a single support surface 162A configured to overlay at least a portion of a first bladder 120 to support the head. A middle section of the headrest 118 includes a first portion that curves upward along a concave arc and extends away from the top section to a second portion of the middle section defining a curved support surface. The second portion of the middle section has a generally horizontal support surface and extends from the first portion to a third portion of the middle section. The third portion of the middle section curves downward along a concave arc and extends away from the second portion of the middle section to a bottom section defining a curved support surface. The middle section defines three support surfaces 162B, 162C, 162D configured to support a second, third, and fourth bladder 120, respectively. The bottom section of the headrest 118 extends from the third portion of the middle section to a bottom end of the headrest. The bottom section curves downward from the third portion of the middle section along a concave arc that is continuous with the concave arc of the third portion of the middle section defining a curved support surface. The bottom section defines a single support surface 162E configured to receive at least a portion of a fifth bladder 120. Additionally, each support surface 162A-E may define a hole 169A-E extending through the support surface. A portion of each hole 169A-E is defined by a respective port 171A-E extending downward from a bottom of a respective support surface 162A-E. Each port 171A-E is configured to receive a tube 173 of a bladder 120 to mount the bladder on the support surface 162A-E. In this position, an inflatable cell 175 of the bladder 120 sits on top of the support surface 162A-E. The tube 173 is connectable to one of the passages 150A-G for receiving air pressure to inflate the cell.

Referring to FIGS. 30-33, an alternative embodiment of a headrest is generally indicated at 218. The headrest 218 is configured for non-pneumatic use such that bladders are not disposed on the headrest. Rather, support surface 262 is responsive to the weight of the patient's head and neck to properly position the patient's head and neck on the headrest 218. The support surface 262 defines a top section, a middle section, and a bottom section. The top section is configured to support a patient's head, the middle section is configured to support the patient's neck, and the bottom section is configured to support the patient's lower neck and upper T-spine. A first portion of the top section has a generally concave support surface to fit the patient's convex cranium. A second portion of the top section curves upward along a concave arc from the first portion and extends to the middle section of the headrest 218 defining a curved support surface. The second portion is narrow and supports the cervical spine bony structures only, hence allowing the lateral soft tissue where the lymphatic channels pass through to sag downward so that the shape of these lymphatic channels is least disturbed under the influence of the engagement of the headrest 218 with the patient's bones. The middle section of the headrest 218 includes a first portion that curves upward along a concave arc and extends away from the top section to a second portion of the middle section defining a curved support surface. The second portion of the middle section has a generally convex support surface to support the flexed cervical neck and extends from the first portion to a third portion of the middle section. The third portion of the middle section curves downward along a concave arc and extends away from the second portion of the middle section to the bottom section defining a curved support surface. The bottom section of the headrest 218 extends from the third portion of the middle section to a bottom end of the headrest. The bottom section curves downward from the third portion of the middle section along a concave arc that is continuous with the concave arc of the third portion of the middle section defining a curved support surface. Cushions (not shown) may also be provided on the support surface 262 to support the different sections of the patient's head and neck. A variety of different sized cushions may be provided to accommodate patients of different sizes. In one embodiment, a plurality of non-pneumatic headrests of varying sizes and configurations may be provided in a kit to accommodate patients of varying sizes and shapes.

Figure 34:
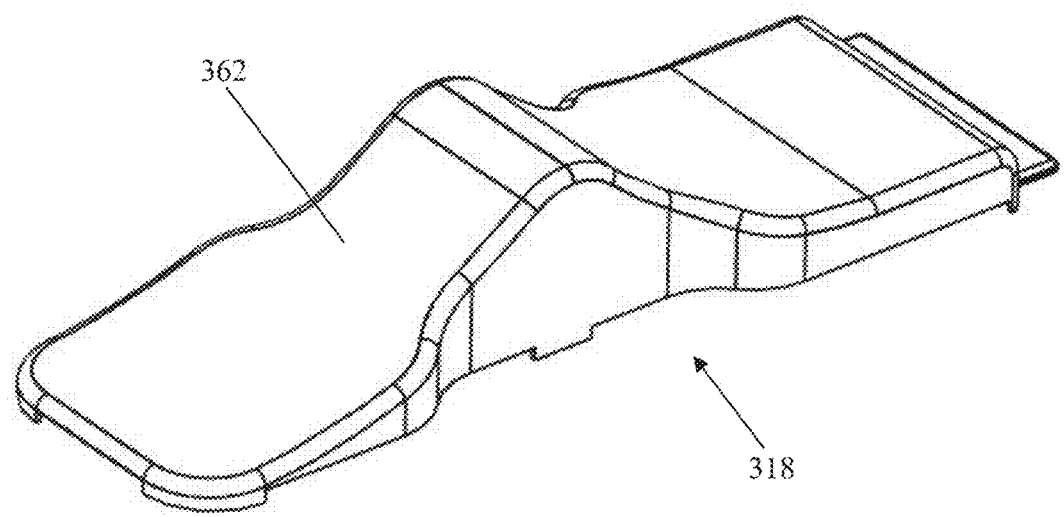
FIG. 34 is a perspective of a headrest of another embodiment.
Figure 35:
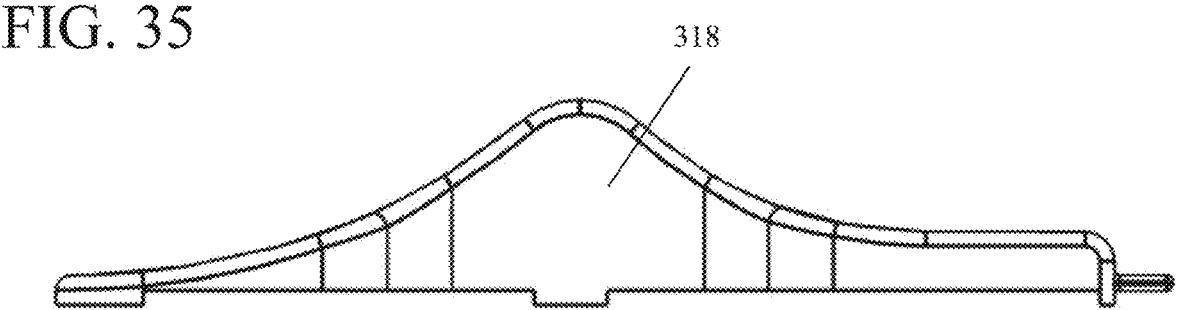
FIG. 35 is a side view of the headrest in FIG. 34.
Figure 36:
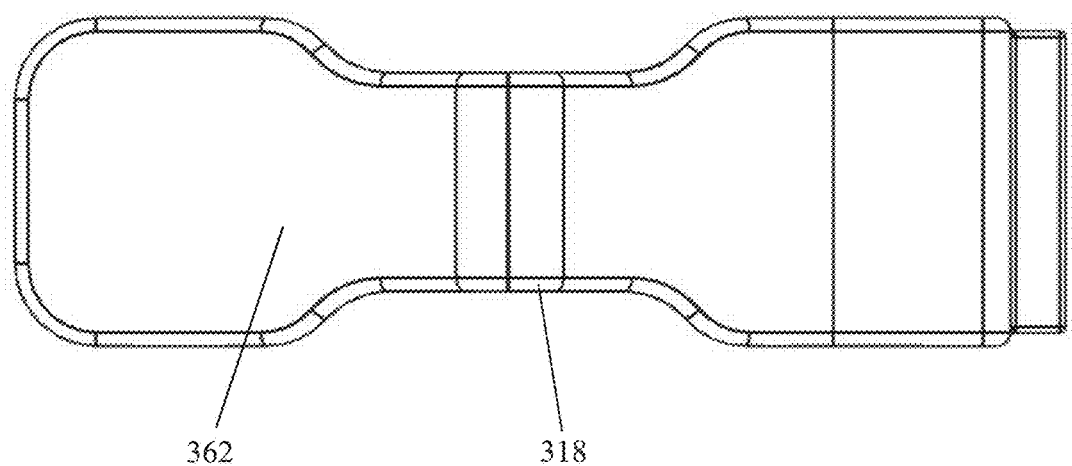
FIG. 36 is a top plan view of the headrest in FIG. 34.

Referring to FIGS. 34-36, another alternative embodiment of a headrest is generally indicated at 318. The headrest 318 is also configured for non-pneumatic use such that bladders are not disposed under the headrest. The headrest 318 has a similar configuration to headrest 218. However, the middle section of support surface 362 has a sharper convex shape for hyperextension of the neck.

Figure 37:
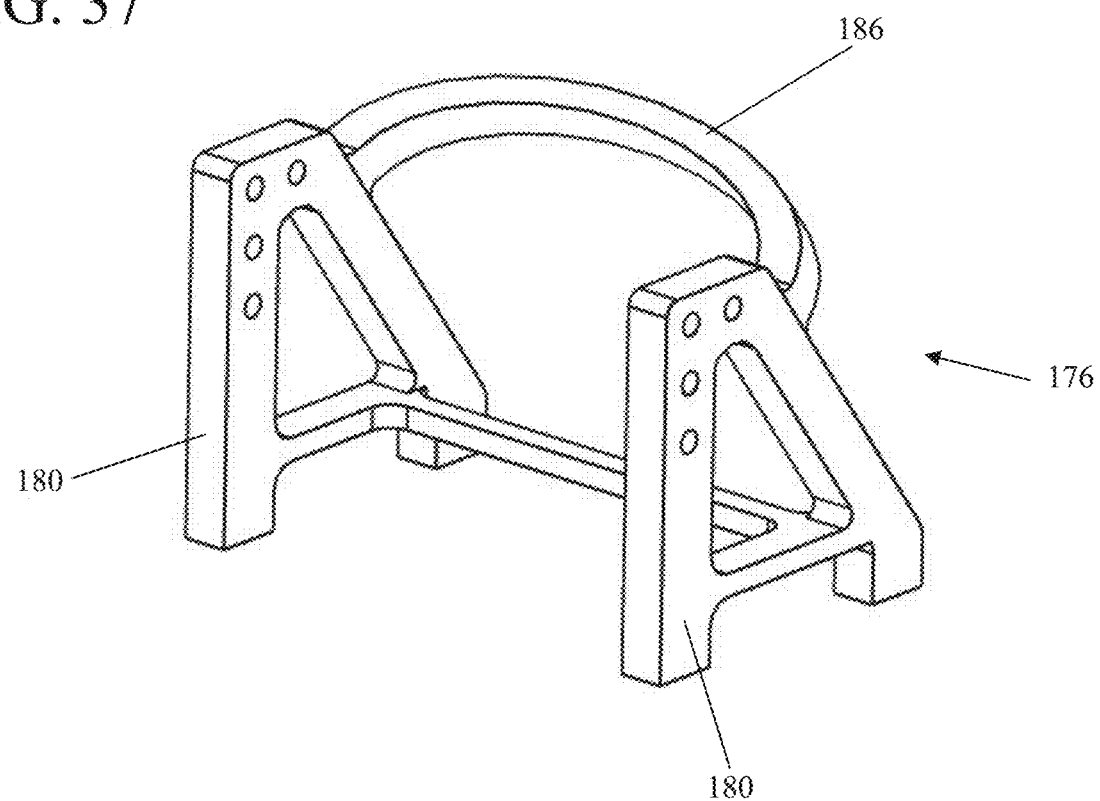
FIG. 37 is a perspective of a head frame of the patient positioning system in FIG. 22.
Figure 38:
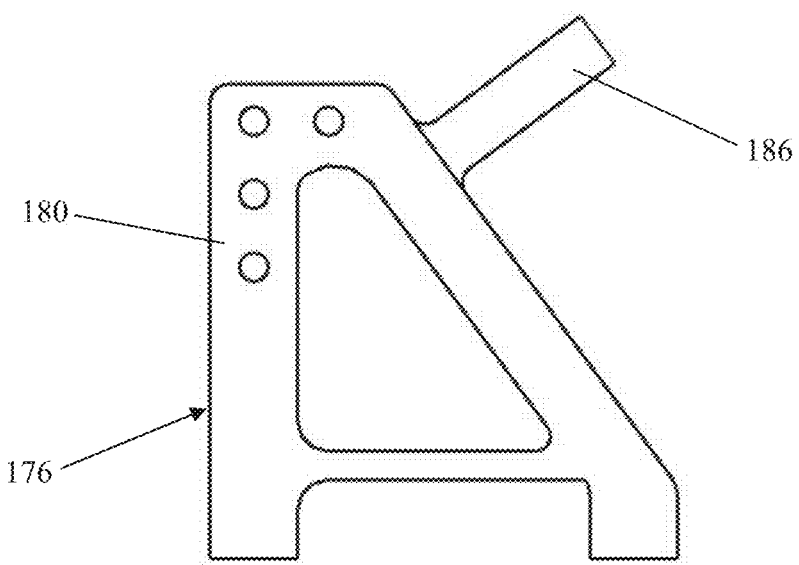
FIG. 38 is a side view of the head frame in FIG. 37.

Referring to FIGS. 37 and 38, a head frame of the head frame assembly 116 is generally indicated at 176. The frame 176 includes a pair of frame members 180 and a frame bar 186 extending between the frame members 180. The frame bar 186 extend upward and backward from the frame members 180 such that the frame bar extends at an angle to vertical. The frame bar 186 is curved to generally accommodate the shape of the patient's head.

Figure 39:
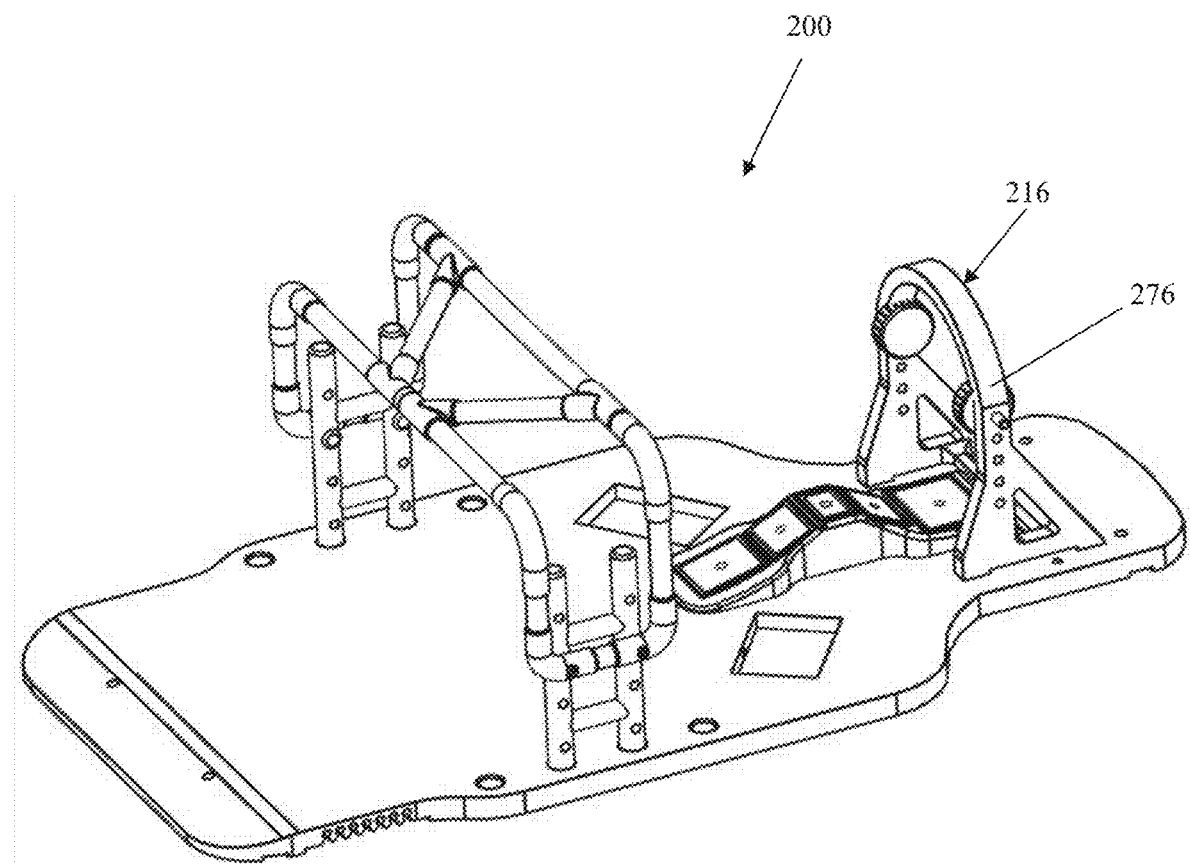
FIG. 39 is a perspective view of a patient positioning system of another embodiment.
Figure 40:
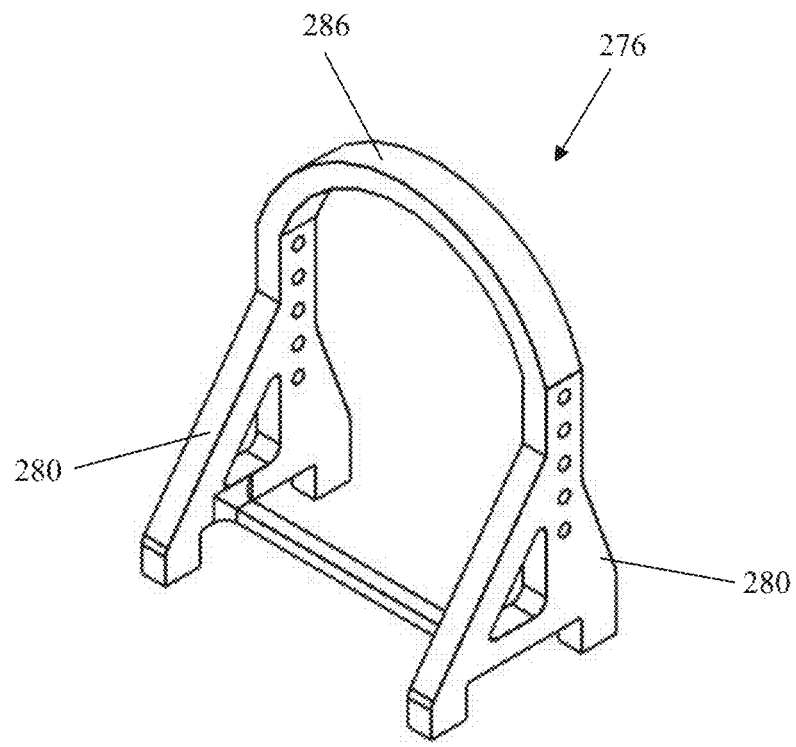
FIG. 40 is a perspective of a head frame of the system in FIG. 39.
Figure 41:
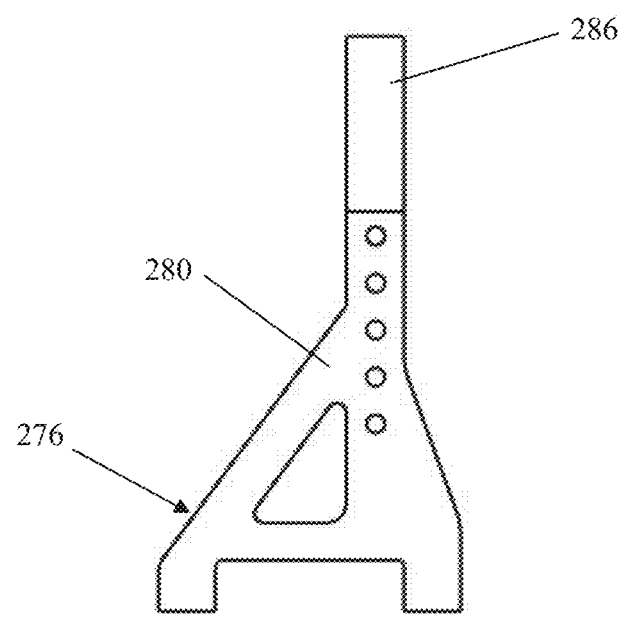
FIG. 41 is a side view of the head frame in FIG. 40.

Referring to FIGS. 39-41, a patient positioning system of another embodiment is generally indicated at 200. The system 200 comprises a head frame assembly 216 including a head frame 276. A frame bar 286 of the head frame 276 extends generally vertically from frame members 280.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A positioning system for positioning a patient for therapy comprising: a support plate including a bottom surface for engaging a support surface to locate the support plate for therapy, and an upper surface; a headrest assembly mounted on the upper surface of the support plate for supporting a head, neck and shoulder area of the patient, the headrest assembly including a plurality of inflatable bladders for adjusting a position of the patient's head, neck and shoulders to selectively position the patient's head and neck for therapy, and a headrest defining a plurality of holes that positions the plurality of inflatable bladders such that top surfaces of the inflatable bladders are exposed through the holes in the headrest for directly engaging the patient, wherein the plurality of inflatable bladders includes a first bladder, a second bladder, and a third bladder centered about and disposed on a central longitudinal axis of the support plate and spaced apart from each other along the central longitudinal axis, wherein the first bladder comprises a single bladder, the second bladder comprises a single bladder, and the third bladder comprises a single bladder.

2. The positioning system of claim 1, wherein the first bladder is configured to adjust a position of the patient's head, and the second bladder is configured to adjust a position of the patient's neck.

3. The positioning system of claim 1, wherein the plurality of inflatable bladders includes the first bladder configured to adjust a position of the patient's head, the second bladder configured to adjust a position of the patient's upper C-spine, the third bladder configured to adjust a position of the patient's middle C-spine, a fourth bladder configured to adjust a position of the patient's lower C-spine, and a fifth bladder configured to adjust a position of the patient's upper T-spine, the fourth and fifth bladder being disposed on the central longitudinal axis, wherein the fourth bladder comprises a single bladder and the fifth bladder comprises a single bladder.

4. The positioning system of claim 3, further comprising a sixth bladder configured to adjust a left shoulder of the patient and a seventh bladder configured to adjust a right shoulder of the patient.

5. The positioning system of claim 3, wherein the first inflatable bladder has a horizontal top surface, the second inflatable bladder has an angled top surface, the third inflatable bladder has a horizontal top surface, the fourth inflatable bladder has an angled top surface, and the fifth inflatable bladder has an angled top surface.

6. The positioning system of claim 1, wherein the support plate defines a plurality of passages extending through the support plate, each inflatable bladder being in fluid communication with one of the passages.

7. The positioning system of claim 1, wherein the headrest includes a top section, a middle section, and a bottom section, the middle section being raised above the top and bottom sections.

8. The positioning system of claim 7, wherein each section defines at least one of a support surface and an opening.

9. The positioning system of claim 7, wherein the middle section is narrower than the top and bottom sections along a direction extending orthogonally to a longitudinal axis of the headrest assembly, to minimize a deformation of lateral neck soft tissue where lymphatic channels pass through.

10. The positioning system of claim 7, wherein the top section defines a single support surface, and the middle section includes a first portion curving upward along a concave arc and extending away from the top section to a second portion of the middle section defining a curved support surface.

11. The positioning system of claim 10, wherein the second portion of the middle section defines a central support surface of the headrest and extends from the first portion of the middle section to a third portion of the middle section, and wherein the third portion of the middle section curves downward along a concave arc and extends away from the second portion of the middle section to a bottom section defining a curved support surface.

12. The positioning system of claim 11, wherein the bottom section of the headrest extends from the third portion of the middle section to a bottom end of the headrest, the bottom section curving downward from the third portion of the middle section along a concave arc that is continuous with the concave arc of the third portion of the middle section defining a curved support surface.

13. The positioning system of claim 1, further comprising a head frame assembly mounted on the upper surface of the support plate, wherein the head frame assembly includes a frame and a pair of adjustable pads movably mounted on the frame to prevent head roll motion.

14. The positioning system of claim 1, wherein the system is configured as a maskless positioning system such that a mask covering the patient's face is not utilized to position the patient.

15. The positioning system of claim 1, further comprising a plurality of headrest assemblies each having a different size or construction.

16. The positioning system of claim 1, wherein the system is configured to support a patient's head, neck, and shoulder area in a radiation therapy device, and selectively adjust a position of the patient's head, neck, and shoulder area using the plurality of inflatable bladders to reproduce patient head and neck positioning for image-guided radiotherapy (IGRT) of the patient's head and neck area.

17. The positioning system of claim 1, wherein the system is configured to selectively adjust the position of the patient's head and neck area to match a reference position from a reference image, wherein the reference image is a computed tomography (CT) scan or a digitally reconstructed radiography (DRR).

18. The positioning system of claim 17, wherein the system is configured for automatically inflating and deflating the plurality of bladders to adjust the position of the patient's head and neck area to match a reference position in a reference image using image processing and machine learning software.

\* \* \* \* \*